(12) United States Patent
Dieu-Nosjean et al.

(10) Patent No.: US 11,385,231 B2
(45) Date of Patent: Jul. 12, 2022

(54) METHODS FOR PREDICTING THE SURVIVAL TIME OF PATIENTS SUFFERING FROM A LUNG CANCER

(71) Applicants: INSERM (INSTITUT NATIONAL DE LA SANTE ET DE LA RECHERCHE MEDICALE), Paris (FR); UNIVERSITE PARIS DESCARTES, Paris (FR); SORBONNE UNIVERSITE, Paris (FR); UNIVERSITE PARIS DIDEROT-PARIS 7, Paris (FR); ASSISTANCE PUBLIQUE-HOPITAUX DE PARIS (ADHP), Paris (FR)

(72) Inventors: Marie-Caroline Dieu-Nosjean, Paris (FR); Wolf Herdman Fridman, Paris (FR); Catherine Sautes-Fridman, Paris (FR); Priyanka Devi, Paris (FR)

(73) Assignees: INSERM (INSTITUT NATIONAL DE LA SANTE ET DE LA RECHERCHE SCIENTIFIQUE), Paris (FR); UNIVERSITE DE PARIS, Paris (FR); SORBONNE UNIVERSITE, Paris (FR); ASSISTANCE PUBLIQUE-HOPITAUX DE PARIS (APHP), Paris (FR)

( * ) Notice: Subject to any disclaimer, the term of this patent is extended or adjusted under 35 U.S.C. 154(b) by 51 days.

(21) Appl. No.: 15/754,640

(22) PCT Filed: Aug. 26, 2016

(86) PCT No.: PCT/EP2016/070158
§ 371 (c)(1),
(2) Date: Feb. 23, 2018

(87) PCT Pub. No.: WO2017/032867
PCT Pub. Date: Mar. 2, 2017

(65) Prior Publication Data
US 2018/0252720 A1 Sep. 6, 2018

(30) Foreign Application Priority Data
Aug. 27, 2015 (EP) .................................... 15306318

(51) Int. Cl.
*G01N 33/574* (2006.01)
(52) U.S. Cl.
CPC ... *G01N 33/57423* (2013.01); *G01N 2800/52* (2013.01)
(58) Field of Classification Search
None
See application file for complete search history.

(56) References Cited

U.S. PATENT DOCUMENTS

2003/0049696 A1   3/2003   Norment et al.

FOREIGN PATENT DOCUMENTS

| WO | 2012/038068 A2 | 3/2012 |
|----|----------------|--------|
| WO | 2013/107907 A1 | 7/2013 |
| WO | 2015/007625 A1 | 1/2015 |

OTHER PUBLICATIONS

Shimizu et al., 2010, J. Thor. Oncol. vol. 5: 585-590.*
Tao et al., 2012, Lung Cancer vol. 75: 95-101.*
Remark et al., Feb. 2015, Am. J. Respir. Crit. Care vol. 191:377-390.*
Goc et al., 2013, Can. Res. vol. 74: 705-715.*
Dieu-Nosjean et al., 2008, J. Clin. Oncol. vol. 26: 4410-4417.*
Petersen et al., 2006, Cancer, vol. 107: 2866-72.*
Sautas-Fridman et al: "Tumor microenvironment is multifaceted", Cancer and Metastasis Reviews, Kluwer Academic Publishers, DO, vol. 30, No. 1, pp. 13-25, Jan. 28, 2011.
Wolf et al: "Immune infiltration inhuman cancer: prognostic significance and disease control", Current Topic in Microbiology and Immunology, Springer, Berlin, DE, vol. 344, pp. 1-24, Jan. 1, 2011.
Hiraoka et al: "Concurrent infiltration by CD8+ T cells and CD4+ T cells in a favorable prognostic factor in non-small-cell lung carcinoma", British Journal of Cancer, vol. 94, No. 2, pp. 275-280, Jan. 30, 2006.

* cited by examiner

*Primary Examiner* — Amy E Juedes
(74) *Attorney, Agent, or Firm* — WCF IP

(57) ABSTRACT

The present invention relates to methods for predicting the survival time of patients suffering from a lung cancer. In particular, the present invention relates to a method for predicting the survival time of a subject suffering from a lung cancer comprising the steps of i) quantifying the density of regulatory T (Treg) cells in a tumor tissue sample obtained from the subject, ii) quantifying the density of one further population of immune cells selected from the group consisting of TLS-mature DC or TLS-B cells or Tconv cells, CD8+ T cells or CD8+ Granzyme-B+ T cells in said tumor tissue sample, iii) comparing the densities quantified at steps i) and ii) with their corresponding predetermined reference values and iv) concluding that the subject will have a short survival time when the density of Treg cells is higher than its corresponding predetermined reference value and the density of the further population of immune cells is lower than its corresponding predetermined reference value or concluding that the subject will have a long survival time when the density of Treg cells is lower than its corresponding predetermined reference value and the density of the further population of immune cells is higher than its corresponding predetermined reference value.

9 Claims, 17 Drawing Sheets

Figure 2C:
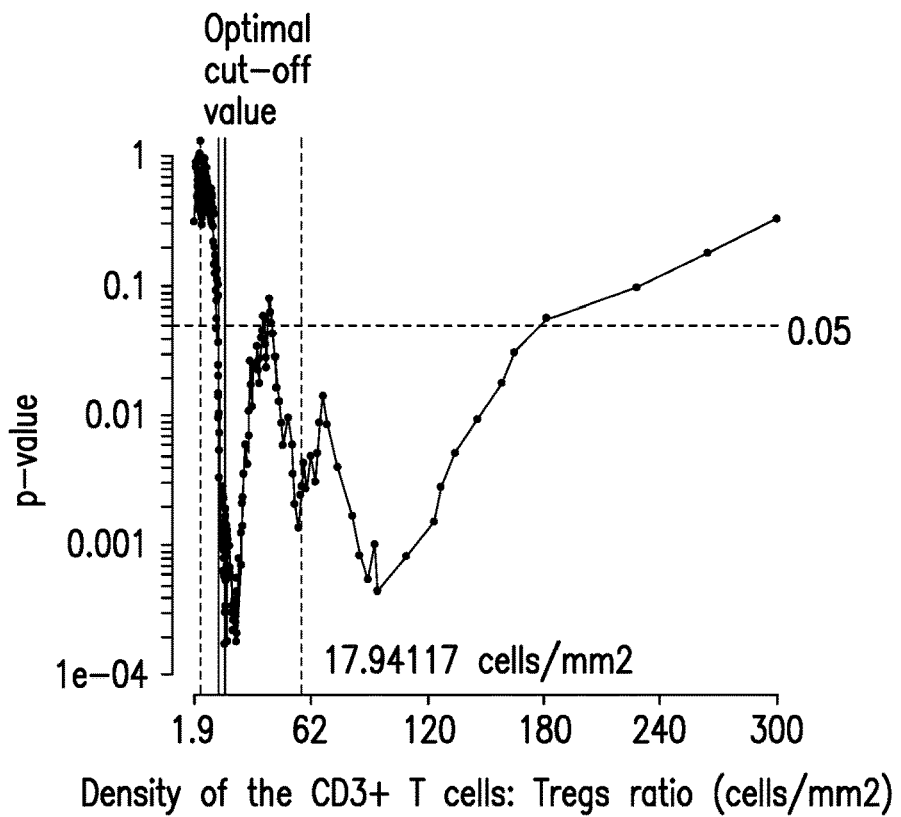
Figure 2D:
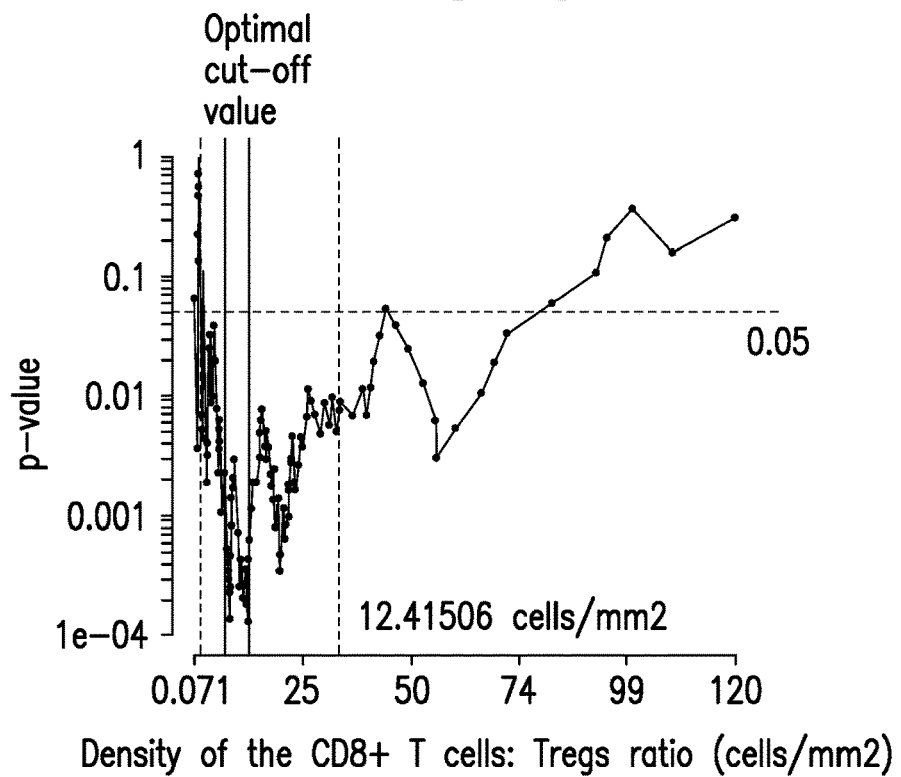
Figure 2E:
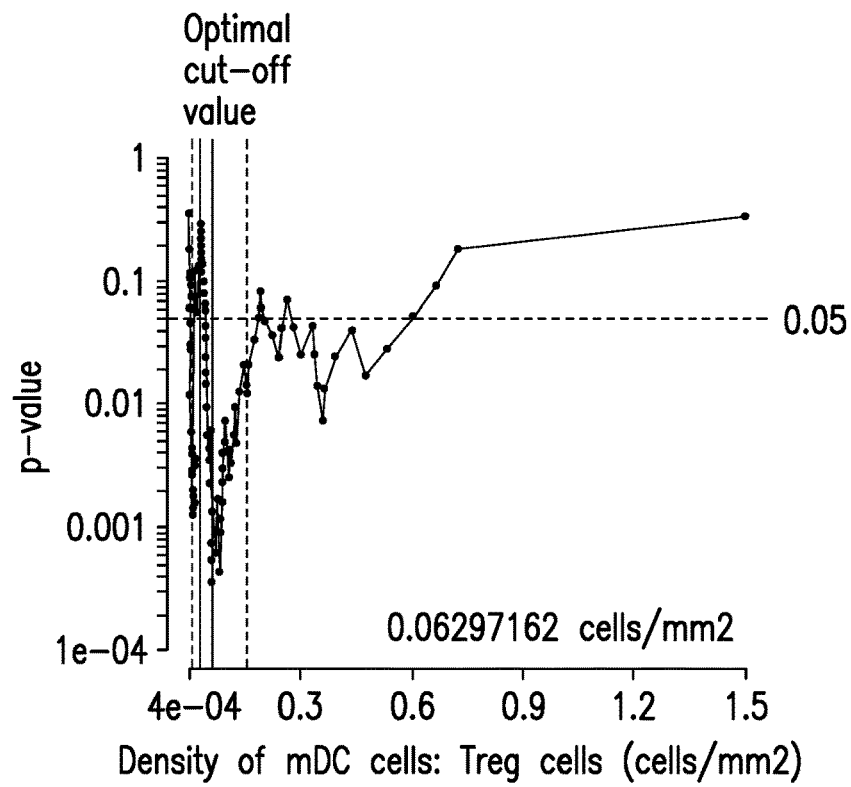
Figure 2F:
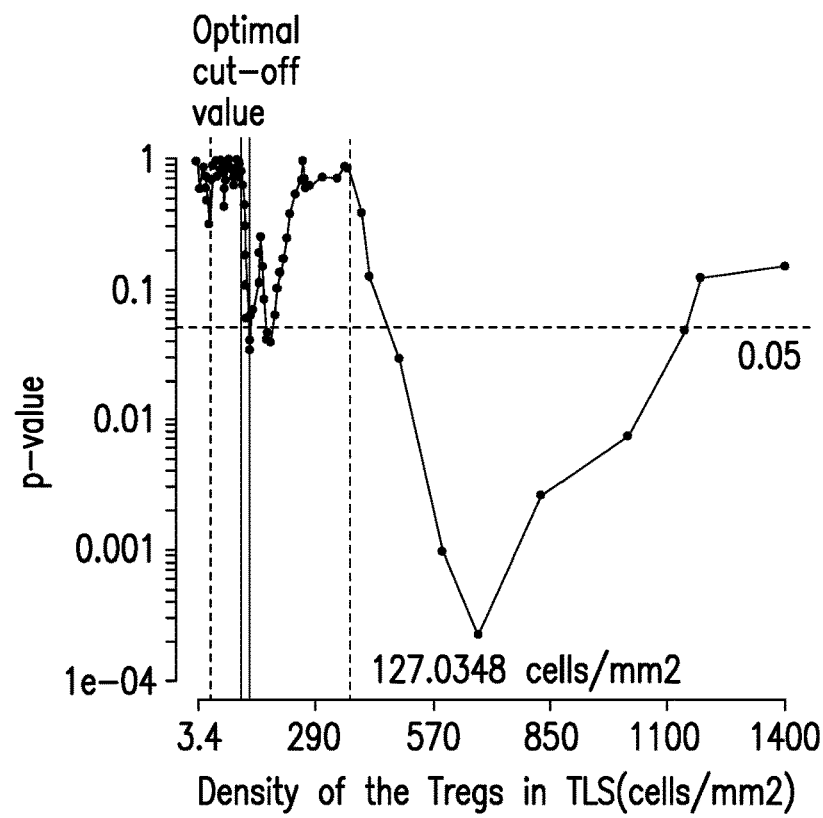
Figure 3A:
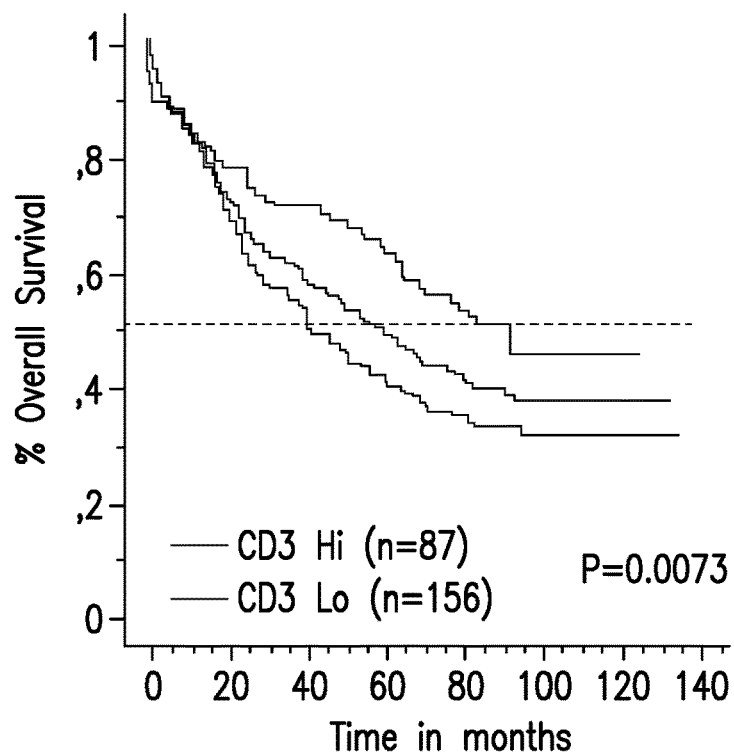
Figure 3B:
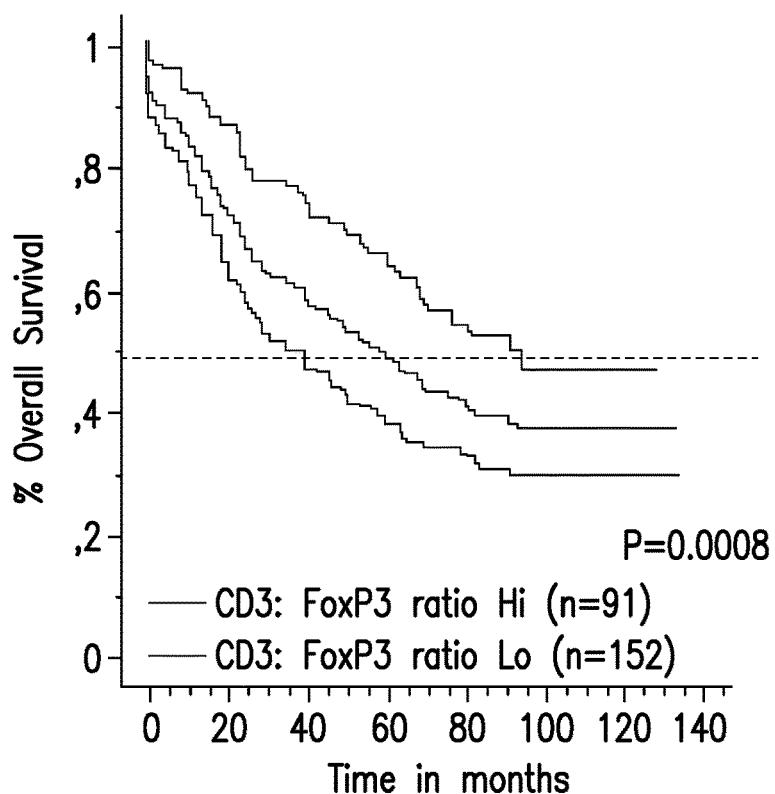
Figure 3C:
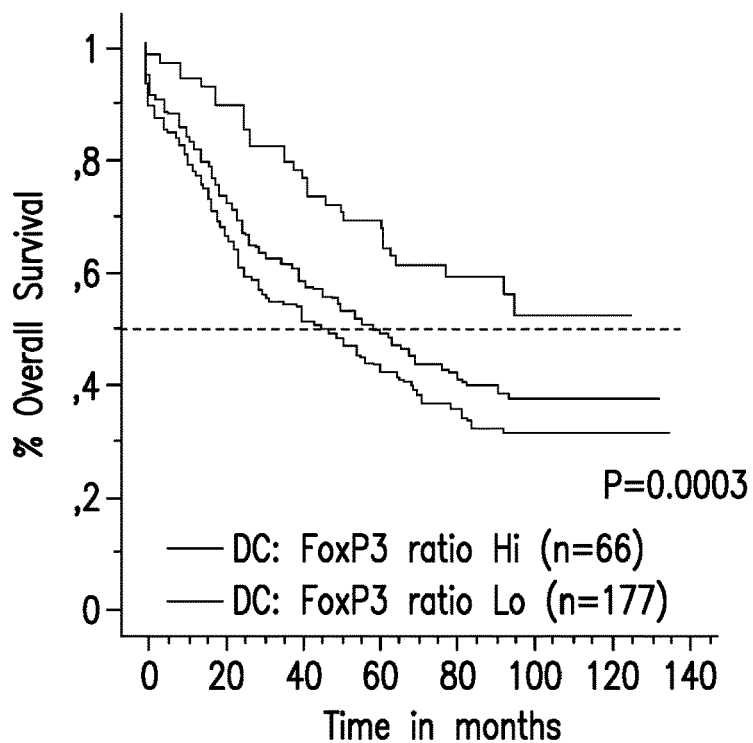
Figure 3D:
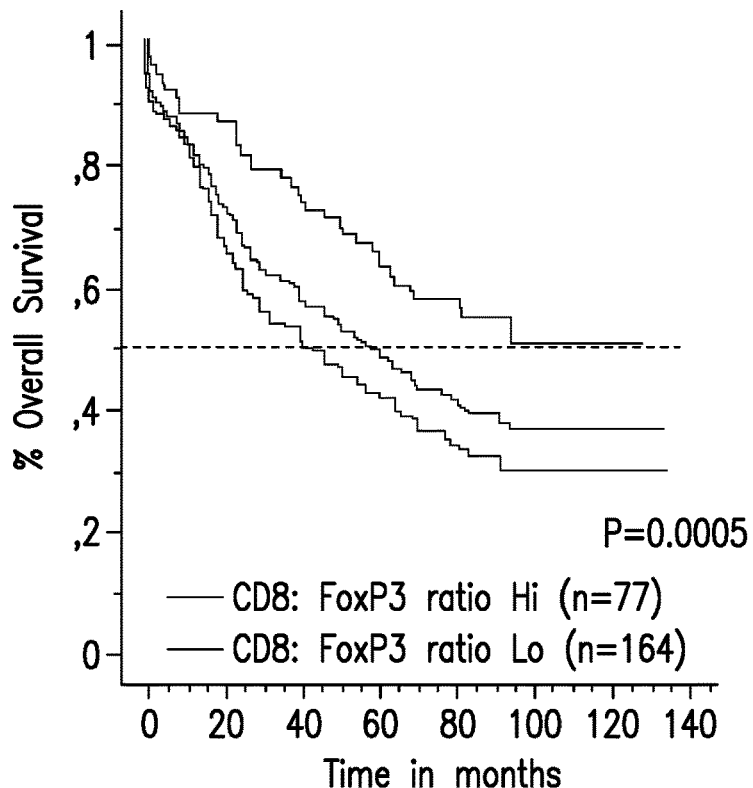

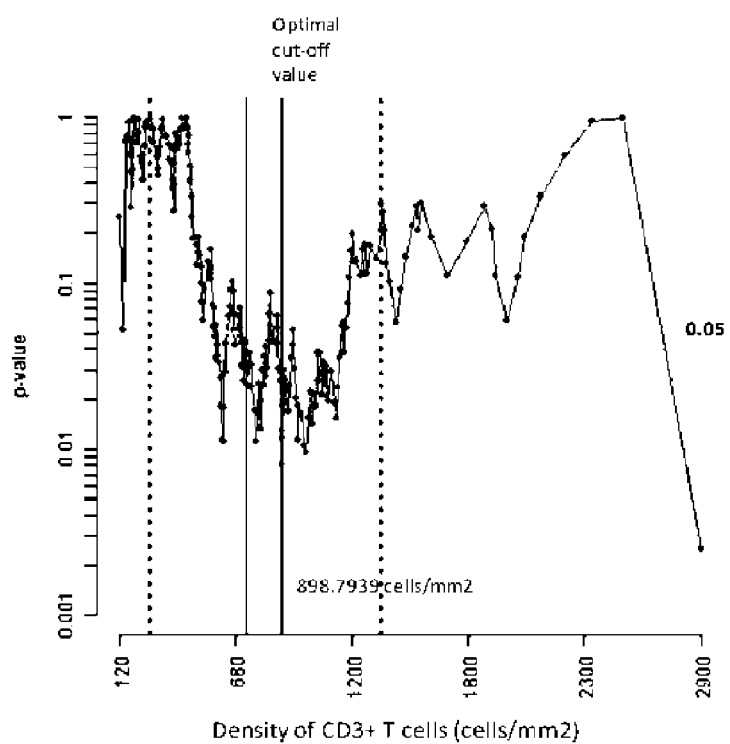
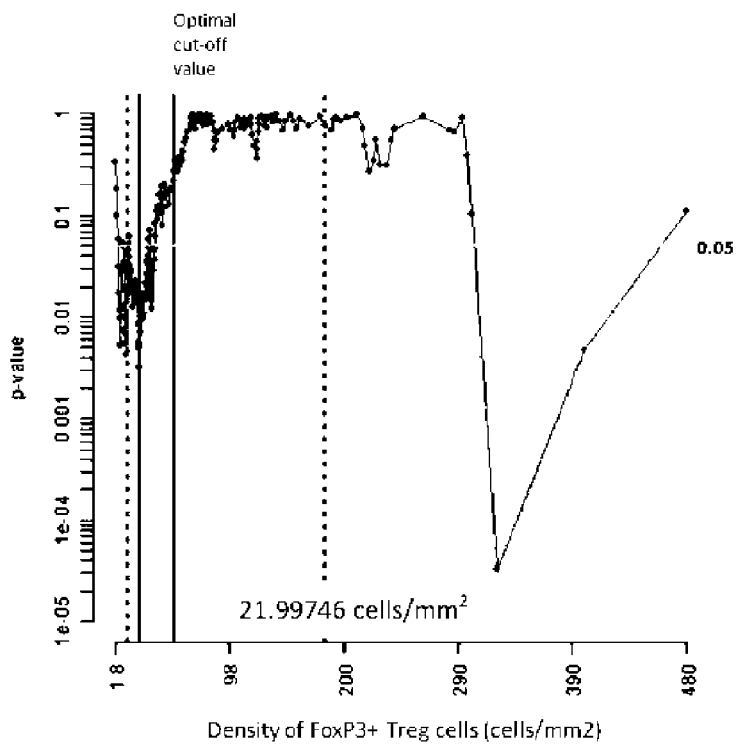
Figures 2A-B

Figure 4A:
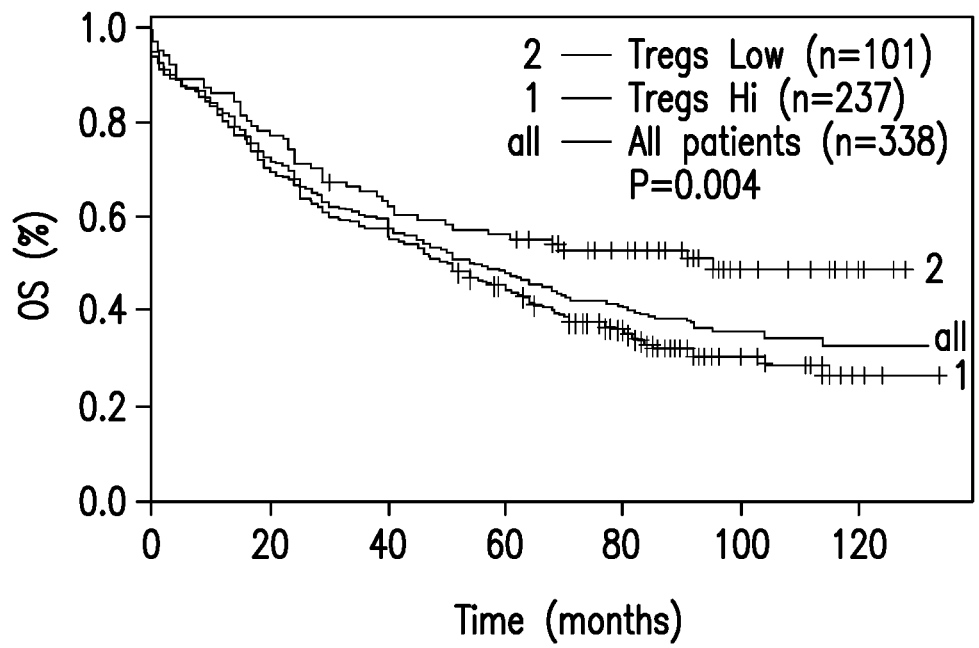
Figure 4B:
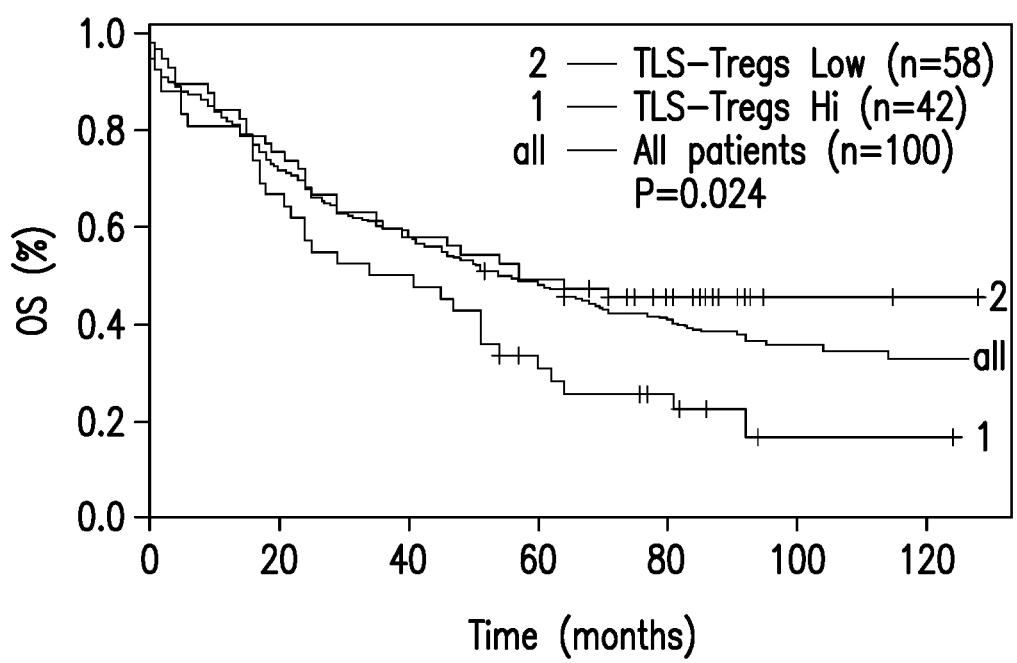
Figure 5A:
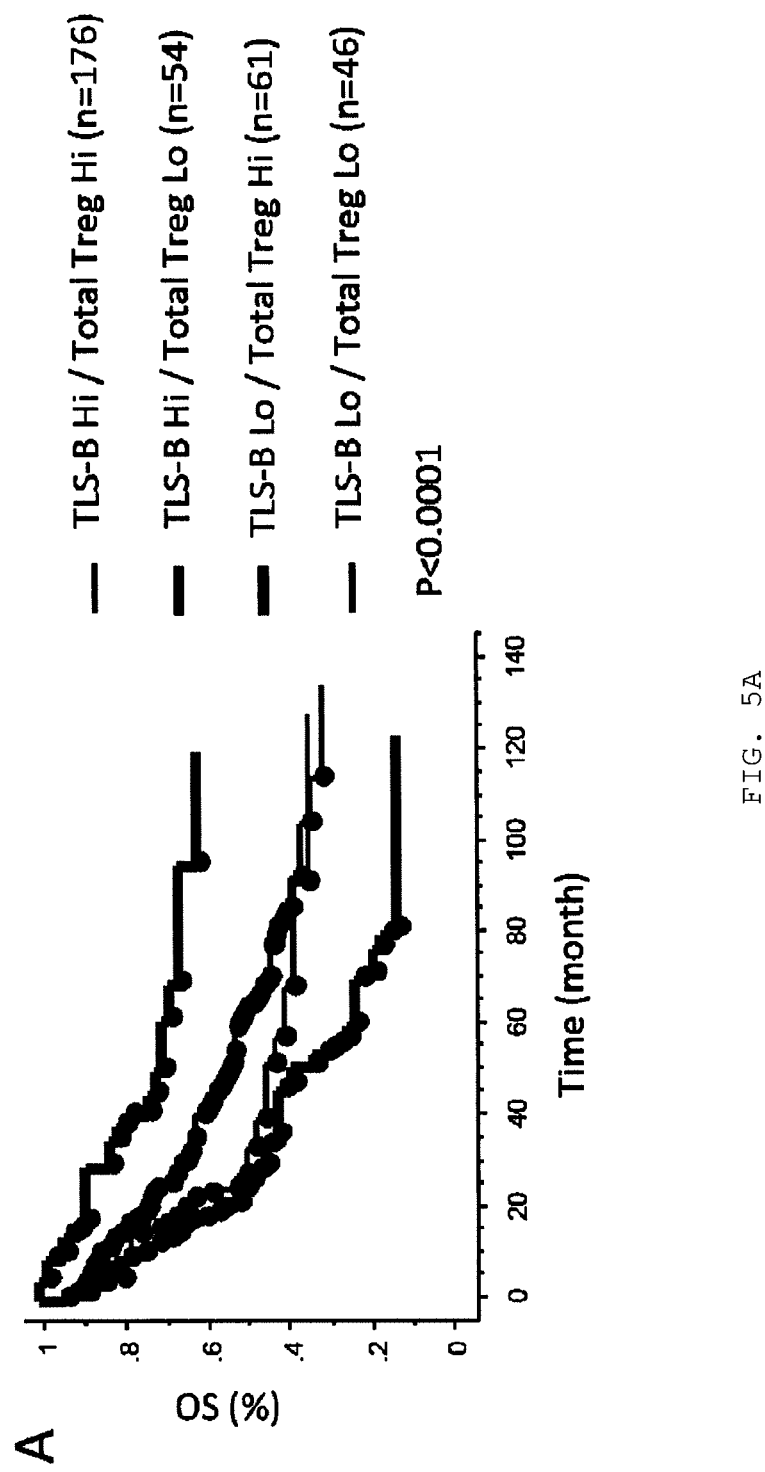
Figure 5B:
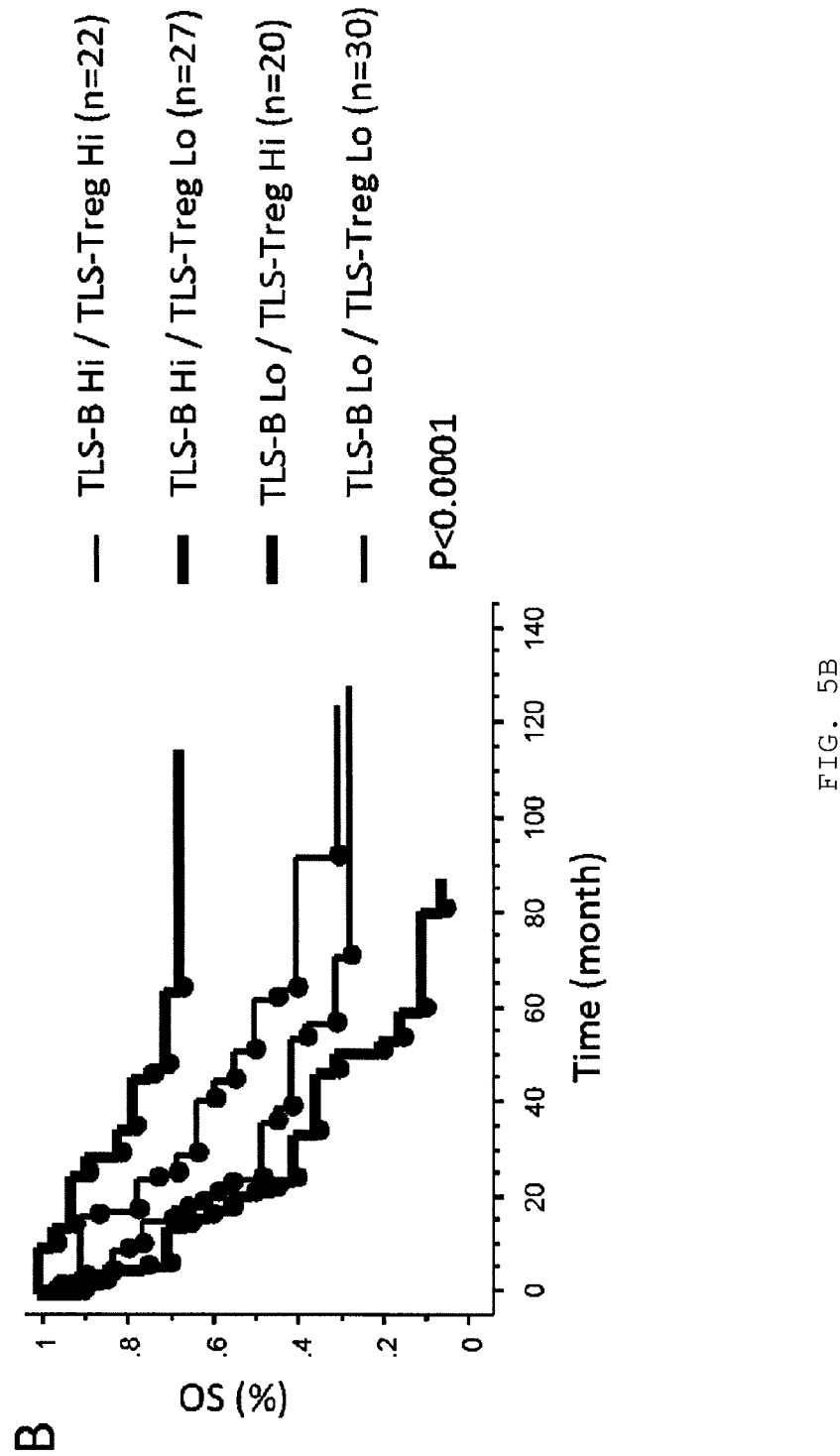
Figure 5C:
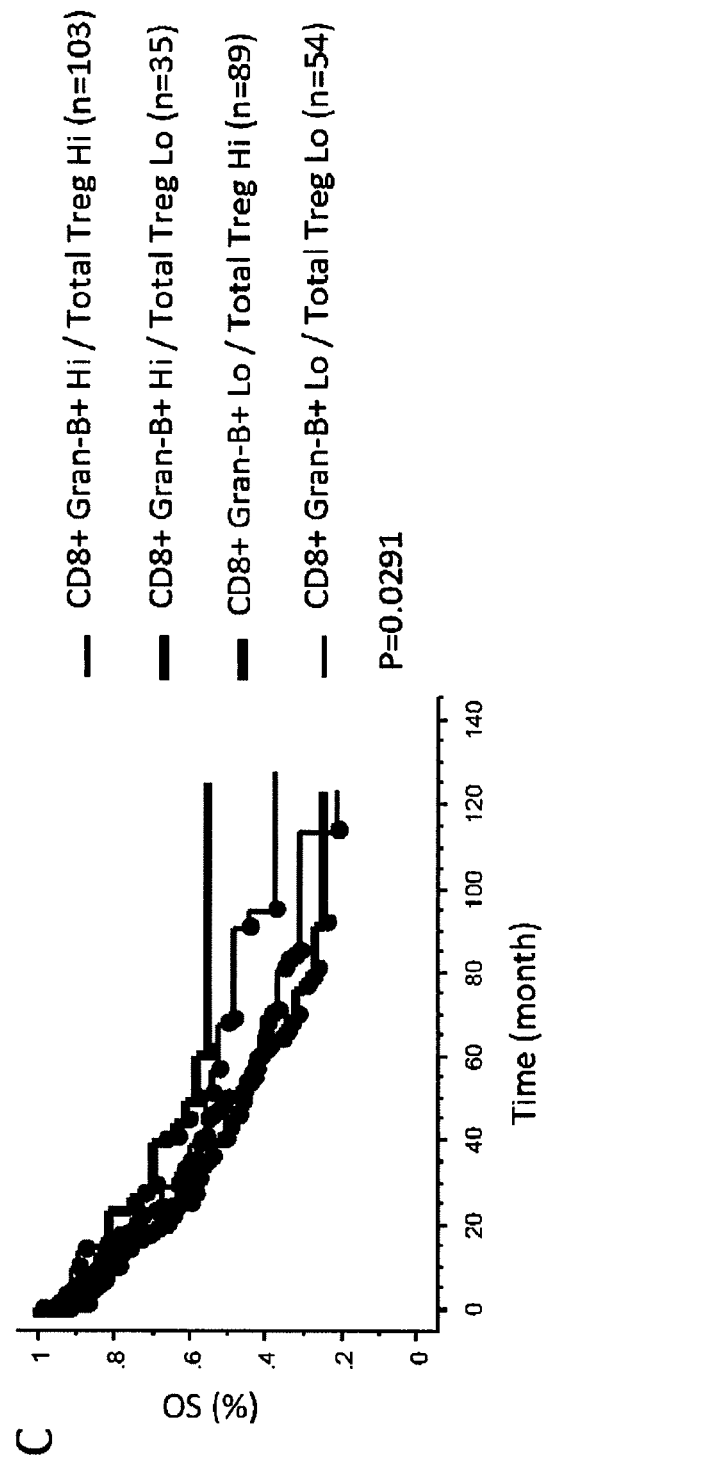
Figure 5D:
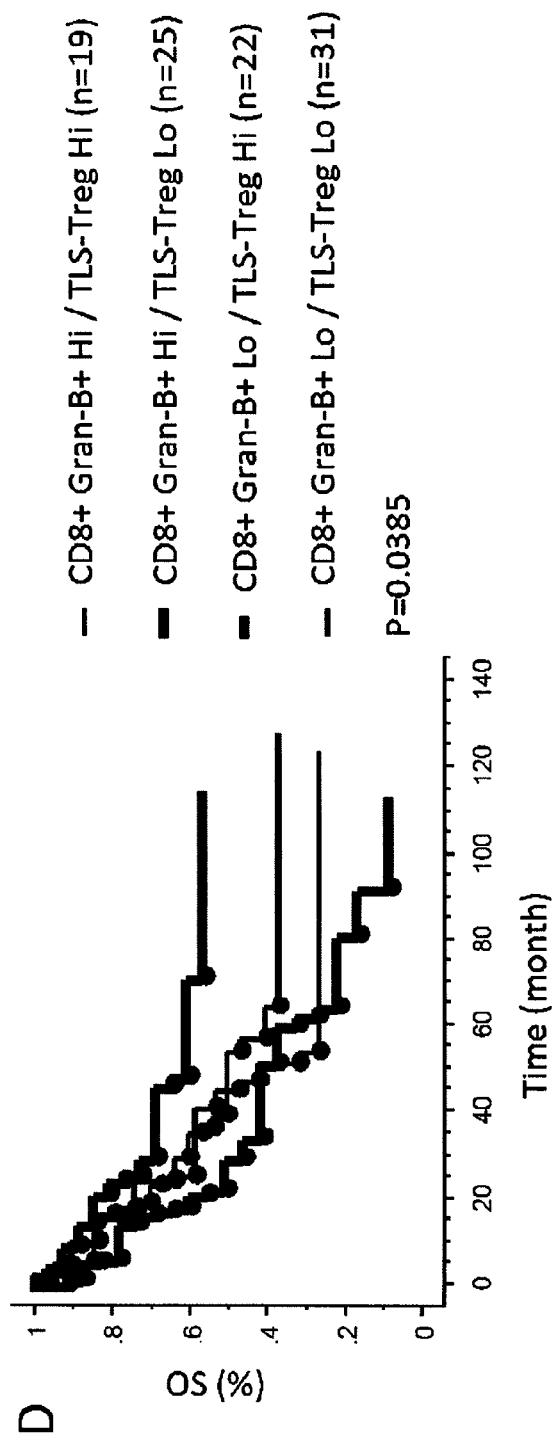

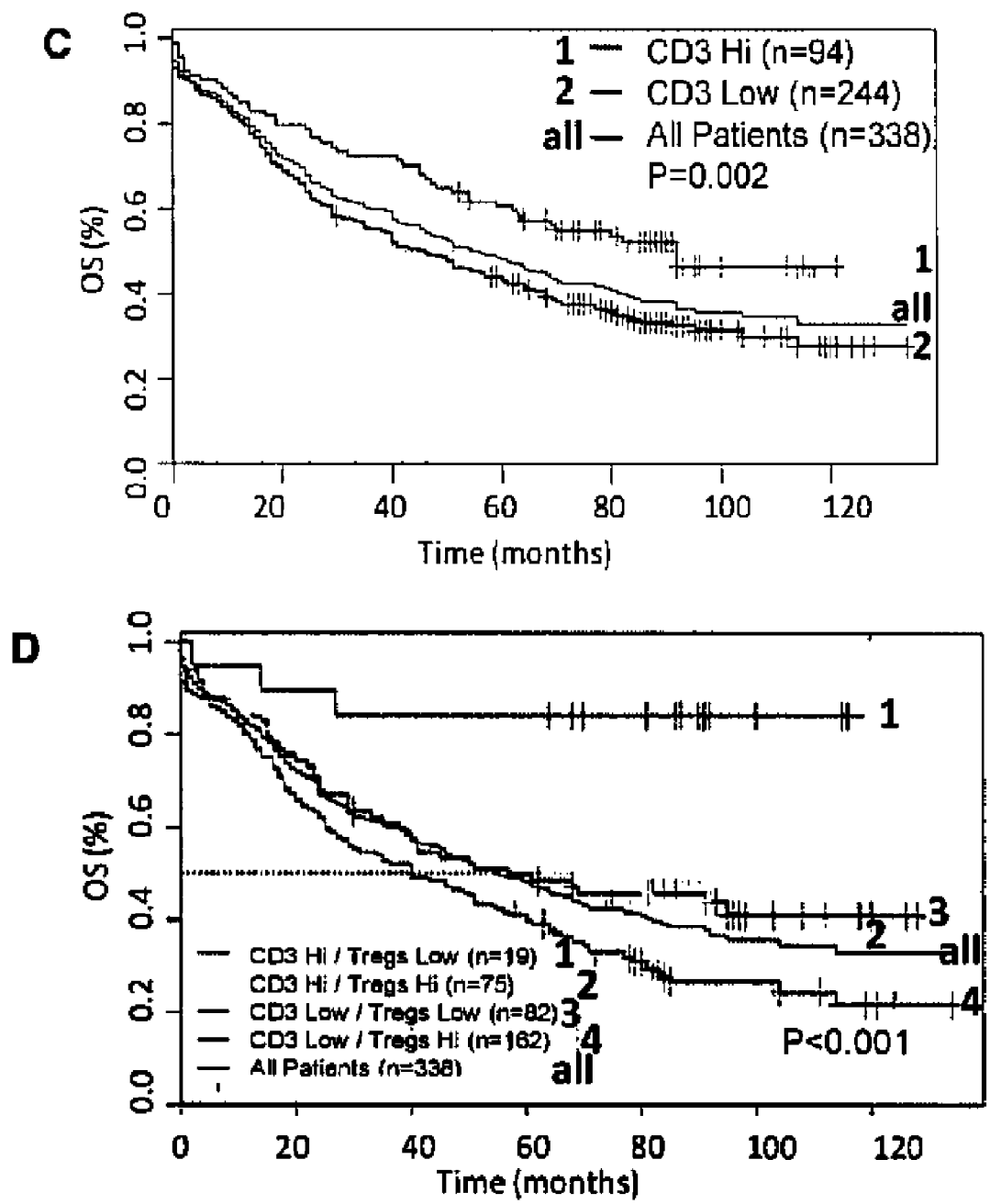
Figure 4 C- D

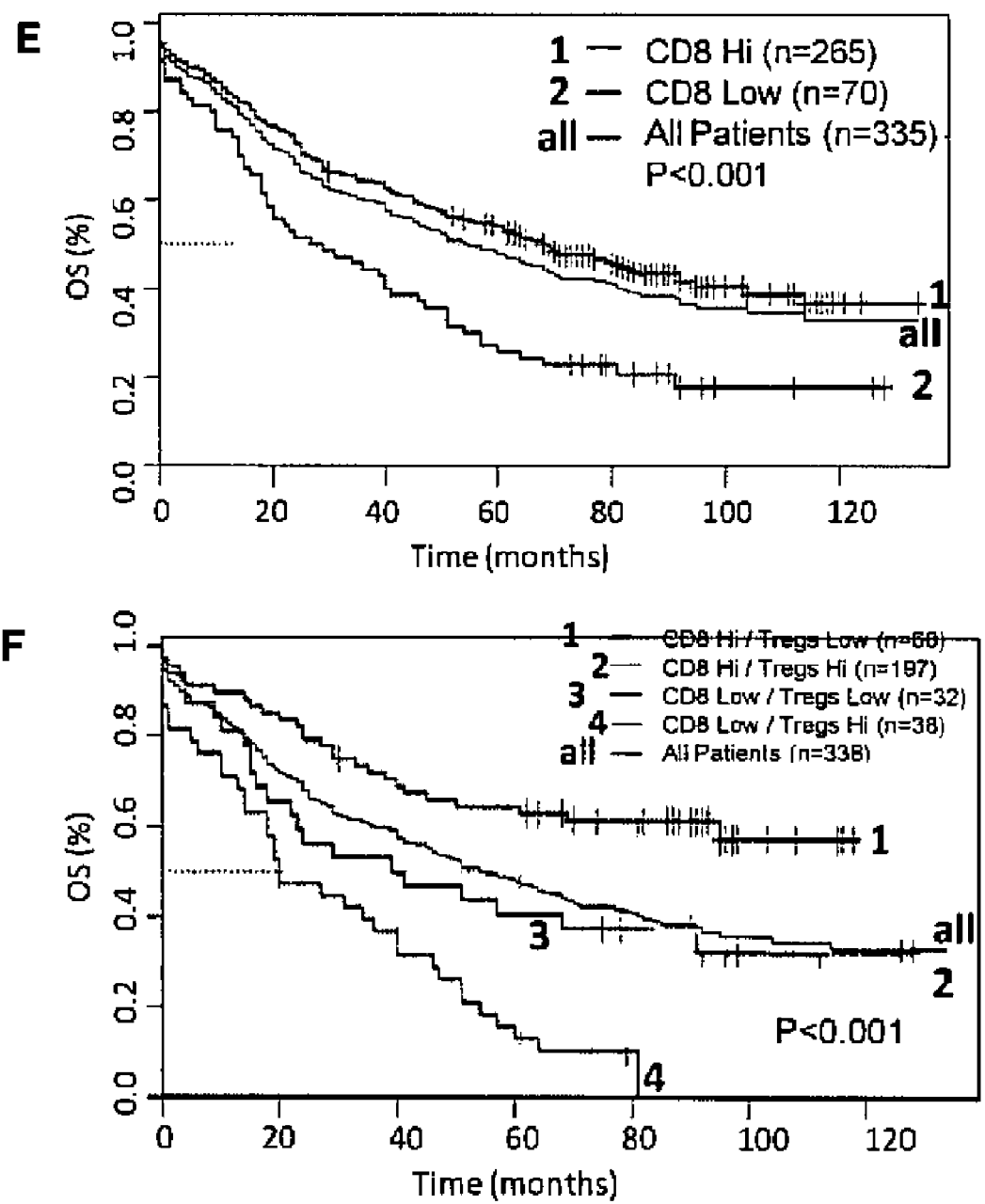
Figure 4 E-F

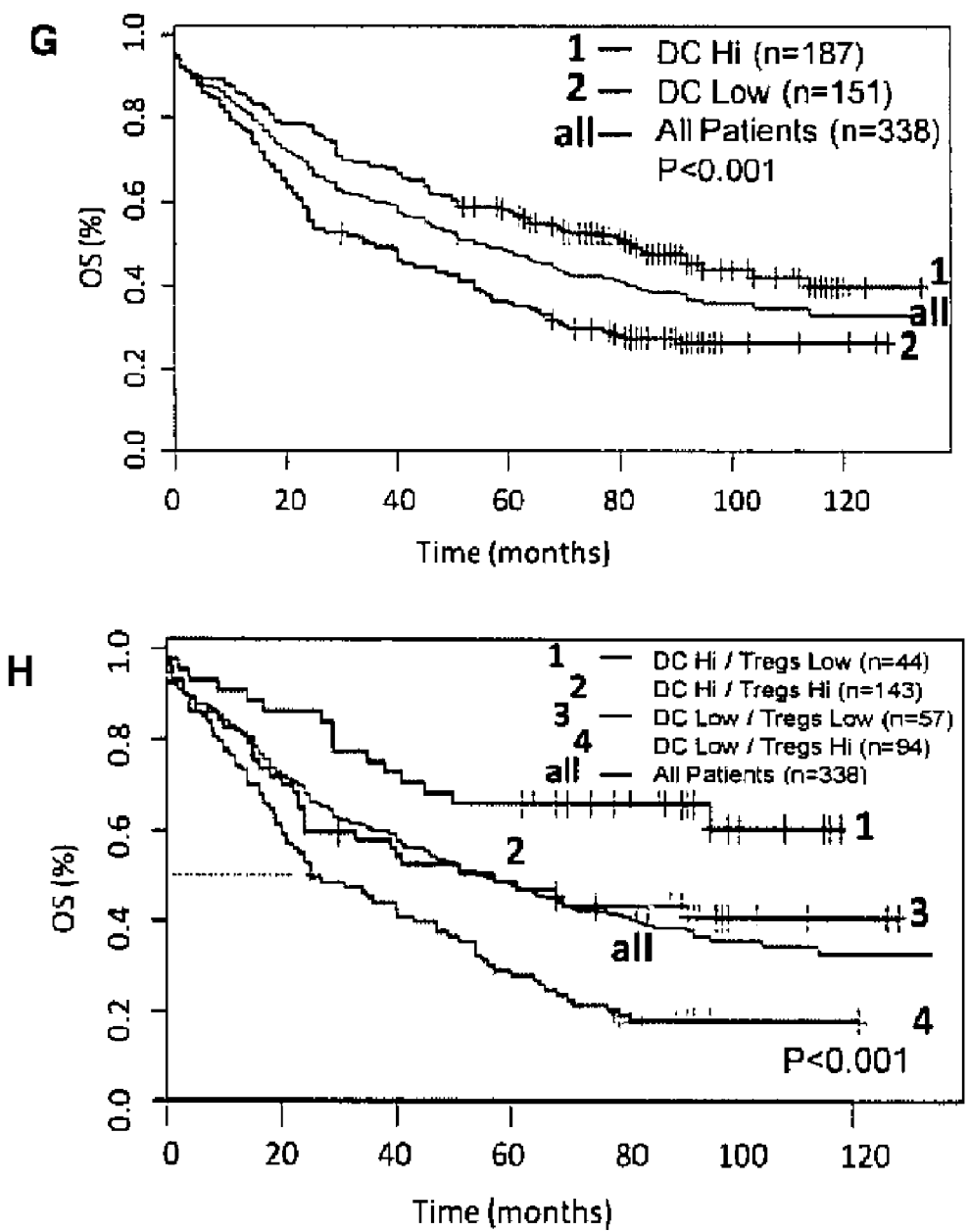
Figure 4 G-H

METHODS FOR PREDICTING THE SURVIVAL TIME OF PATIENTS SUFFERING FROM A LUNG CANCER

FIELD OF THE INVENTION

The present invention relates to methods for predicting the survival time of patients suffering from a lung cancer.

BACKGROUND OF THE INVENTION

As indicated in Dieu-Nosjean et al. (J Clin Oncol 26:4410-4417. 2008), lung cancer is the most common cause of cancer related death in the world. Approximately 80% to 90% of cases involve Non-Small-Cell Lung Cancer (NSCLC), which includes adenocarcinoma and squamous cell carcinoma. Only patients whose tumors can be completely resected have a significant chance of increased survival. However, as many as 30% of patients with stage I disease experience recurrence after surgery. The correlation between tumor-infiltrating immune cells and the prognosis of patients with lung cancer is controversial. A tumor is composed of malignant, stromal, endothelial, and immune cells that form a heterogeneous network and exhibit complex interactions. Although tumor eradication by the immune system is often inefficient, there is evidence that many developing cancers are not ignored by the immune system. Spontaneous tumor regressions occurring concomitantly with autoimmune manifestations and the higher incidence of tumors in immunosuppressed patients are indications of the involvement of the immune system in tumor rejection. Mice deficient in immune functions spontaneously develop tumors. The density of tumor-infiltrating lymphocytes (TILs) with cytotoxic and memory phenotypes is highly predictive of good clinical outcome in many solid tumors.

It is now well established that immune responses can take place at distance of secondary lymphoid organs, in tertiary lymphoid structures (TLS). Dieu-Nosjean et al. have observed that these lymph node-like structures can develop in lung cancer patients. They have been initially named "Tumor-induced Bronchus-Associated Lymphoid Tissues" (Ti-BALT) as they were never found in the non-tumoral tissues of NSCLC patients. Now, the current terminology is "Tertiary Lymphoid Structure" (TLS) or "Tertiary Lymphoid Organ" (TLO). Dieu-Nosjean et al. have demonstrated that the density of mature DC, a population which was selectively detected in TLS, is associated with a favorable clinical outcome in patients with early-stage NSCLC (Dieu-Nosjean et al., J. Clin. Oncol., 2008), and in metastatic stage (Remark et al., Clin Cancer Res. 2013 Jun. 19) suggesting that lung cancer-associated TLS represent an activation site for tumor-specific T cells.

More recently, the team of Dieu-Nosjean also demonstrated that a high density of B cells in TLS (named "TLS-B cells" or "Follicular B cells") correlates with long-term survival of patients with early-stage and advanced-stage NSCLC, in accordance with ongoing humoral immune response in TLS (Germain et al., Am. J. Respir. Crit. Care Med., 2014). The combination of TLS-B cells and TLS-mature DC allowed the identification of NSCLC patients with the best clinical outcome. Moreover, in the TLS the density of germinal center B cells also correlates with the density of plasma cells which may secrete antibodies against endogenous tumor-associated antigens. These data strongly suggest that TLS play a protective role against tumors by promoting an humoral immune response in lung cancer patients (Germain et al., Frontiers Immunol., 2015).

The presence of TLS has been reported in other human tumors including, but is not limited to, colorectal cancer (Coppola et al., Am J Pathol., 2011; 179(1):37-45; McMullen et al., Clin Exp Immunol. 2010; 161(1):81-8), breast cancer (Gobert et al., Cancer Res 2009; 69(5) 2000-2009; Martinet et al., Cancer Res. 2011; 71(17) 5678-87; Gu-Trantien et al., J Clin Invest. 2013; 123(7):2873-92) and melanoma (Martinet et al., Cancer Res. 2011; 71(17) 5678-87; Cipponi et al., Cancer Res. 2012; 72(16):3997-4007) indicating that ectopic lymphoid structures arise in many solid tumors (Dieu-Nosjean et al., Trends Immunol., 2014).

SUMMARY OF THE INVENTION

The present invention relates to methods for predicting the survival time of patients suffering from a lung cancer. In particular, the present invention is defined by the claims.

DETAILED DESCRIPTION OF THE INVENTION

A first object of the present invention relates to a method for predicting the survival time of a subject suffering from a lung cancer comprising the steps of i) quantifying the density of regulatory T (Treg) cells in a tumor tissue sample obtained from the subject, ii) quantifying the density of one further population of immune cells selected from the group consisting of TLS-mature DC or TLS-B cells or CD3+ Tconv cells, CD8+ T cells, or CD8+ Granzyme-B+ T cells in said tumor tissue sample, iii) comparing the densities quantified at steps i) and ii) with their corresponding predetermined reference values and iv) concluding that the subject will have a short survival time when the density of Treg cells is higher than its corresponding predetermined reference value and the density of the further population of immune cells is lower than its corresponding predetermined reference value or concluding that the subject will have a long survival time when the density of Treg cells is lower than its corresponding predetermined reference value and the density of the further population of immune cells is higher than its corresponding predetermined reference value.

As used herein, the term "lung cancer" includes, but is not limited to all types of lung cancers at all stages of progression like lung carcinomas metastatic lung cancer, non-small cell lung carcinomas (NSCLC) such as lung adenocarcinoma, squamous cell carcinoma, or small cell lung carcinomas (SCLC). In some embodiments, the subject suffers from a non-small cell lung carcinomas (NSCLC).

The method is particularly suitable for predicting the duration of the overall survival (OS), progression-free survival (PFS) and/or the disease-free survival (DFS) of the cancer subject. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they have become cancer-free (achieved remission). DSF gives more specific information and is the number of people with a particular cancer who achieve remission. Also, progression-free survival (PFS) rates (the number of people who still have cancer, but their disease does not progress) include people who may have had some success with treatment, but the cancer has not disappeared completely. As used herein, the expression "short survival time" indicates that the subject will have a survival time that will be lower than the median (or mean) observed in the general population of subjects suffering from said cancer. When the subject will have a short survival time, it is meant that the subject will have a "poor prognosis". Inversely, the expression "long survival time" indicates that the subject will have a survival time that will be higher than the median (or mean) observed in the general population of subjects suffering from said cancer. When the subject will have a long survival time, it is meant that the subject will have a "good prognosis".

As used herein, the term "tumor tissue sample" has its general meaning in the art and encompasses pieces or slices of tissue that have been removed including following a surgical tumor resection. The tumor tissue sample can be subjected to a variety of well-known post-collection preparative and storage techniques (e.g., fixation, storage, freezing, etc.) prior to determining the cell densities. Typically the tumor tissue sample is fixed in formalin and embedded in a rigid fixative, such as paraffin (wax) or epoxy, which is placed in a mould and later hardened to produce a block which is readily cut. Thin slices of material can be then prepared using a microtome, placed on a glass slide and submitted e.g. to immunohistochemistry (IHC) (using an IHC automate such as BenchMark® XT or Autostainer Dako, for obtaining stained slides).

As used herein, the term "tumor-induced lymphoid structure" has its general meaning in the art and refers to the organization of tumor-infiltrating leukocytes into lymph-node like structure (also called TLS or TLO) in the stroma of the tumor mass and, is composed of mature DC-T cell clusters (T-cell areas) and B-cell follicles (B-cell areas). Typically, depending on the tumor section, only one out of the two areas or both areas can be observed. This organization was called Ti-BALT for Tumor-induced Bronchus-Associated Lymphoid Tissues in lung cancer (Dieu-Nosjean et al., J. Clin. Oncol., 2008).

As used herein, the term "regulatory T cell" or "Treg cell" has its general meaning in the art and refers to a subset of T helper cells endowed with a given antigen specificity imprinted by the TCR it expresses and with regulatory properties defined by the ability to suppress the response of conventional T lymphocytes or other immune cells. Such response are known in the art and include, but is no limited to, cytotoxic activity against antigen-presenting target cells and secretion of different cytokines. Different types of Treg cells exist and include, but are not limited to, inducible and thymic-derived Treg cells, as characterized by different phenotypes such as CD4+CD25+/high, CD4+CD25+/highCD127−/low alone or in combination with additional markers that include, but are not limited to, FoxP3, neuropilin-1 (CD304), glucocorticoid-induced TNFR-related protein (GITR), cytotoxic T-lymphocyte-associated protein 4 (CTLA-4, CD152). Typically, a Treg cell according to the invention is a CD3+FoxP3+ T cell. Typically, the density of Treg cells can be measured at several areas of the tumor: whole tumor, TLS, and non-TLS areas.

As used herein, the term "TLS-mature dendritic cells" or "TLS-mature DC" or "mature DC" has its general meaning in the art and refers to a population of cells that are professional for the presentation of processed antigens to T cells. Mature dendritic cells infiltrating the tumor are selectively located in contact with T cells, in the T-cell rich areas of the tumor-induced lymphoid structure. Typically, mature DC are characterized by classical expression of markers at their cell surface such as DC-LAMP (i.e. CD208). Typically, a dendritic cell of the present invention is a DC-LAMP+ mature DC.

As used herein, the term "follicular B cell" or "TLS-B cell" has its general meaning in the art and refers to B cell subsets clustered into B-cell follicle of TLS. They are mainly of naïve and germinal center phenotype.

As used herein, the term "conventional T cell" or "Tconv T cell" has its general meaning in the art and refers to CD3+ T cell (including CD4+ cell and CD8+ T cell) with the exception of Treg cell. They are defined by the expression of CD3 and the non/low expression of FoxP3 (CD3+ FoxP3− cell). In some embodiments, Tconv cells are CD3+ T cells.

As used herein, the term "CD8+ Granzyme-B+ T cell" or "CD8+ Gran-B+ T cell" has its general meaning in the art and refers to a subset of CD8+ CD3+ T cells expressing the cytolytic molecule Granzyme B, and having the ability to kill the target cell in a Granzyme B-dependent manner. They are of effector phenotype.

In some embodiments, the density of regulatory T (Treg) cells and the density of TLS-mature DC are quantified at steps i) and ii) respectively.

In some embodiments, the density of regulatory T (Treg) cells and the density of TLS-B cells are quantified at steps i) and ii) respectively.

In some embodiments, the density of regulatory T (Treg) cells and the density of Tconv cells are quantified at steps i) and ii) respectively.

In some embodiments, the density of regulatory T (Treg) cells and the density of CD8+ cells are quantified at steps i) and ii) respectively.

In some embodiments, the density of regulatory T (Treg) cells and the density of CD8+ Gran-B+ T cells are quantified at steps i) and ii) respectively.

In some embodiments, the quantification of densities is determined by IHC.

For example, the quantification of the density of Treg cells is performed by contacting the tumor tissue sample with a binding partner (e.g. an antibody) specific for a cell marker of said cells. Typically, the quantification of density of Treg cells is performed by contacting the tissue tumor tissue sample with both binding partners (e.g. an antibody) specific for FoxP3 (intranuclear marker) and for CD3 (cell surface marker), respectively.

For example, the quantification of the density of TLS-mature DC is performed by contacting the tumor tissue sample with a binding partner (e.g. an antibody) specific for a intracytoplasmic cell marker of said cells. Typically, the quantification of density of TLS-mature DC is performed by contacting the tissue tumor tissue sample with a binding partner (e.g. an antibody) specific for DC-LAMP (CD208, a dot staining).

For example, the quantification of the density of TLS-B cells is performed by contacting the tumor tissue sample with a binding partner (e.g. an antibody) specific for a cell surface marker of said cells. Typically, the quantification of density of TLS-B cells is performed by contacting the tumor tissue sample with a binding partner (e.g. an antibody) specific for CD20.

For example, the quantification of the density of Tconv cells is performed by contacting the tumor tissue sample with a binding partner (e.g. an antibody) specific for a cell marker of said cells, excluding Treg cells. Typically, the quantification of density of Tconv cells (CD3+ FoxP3−) is performed by contacting the tumor tissue sample with both binding partners (e.g. an antibody) specific for CD3 (cell surface marker) and FoxP3 (intranuclear marker), respectively.

For example, the quantification of the density of CD8+ T cells is performed by contacting the tumor tissue sample with a binding partner (e.g. an antibody) specific for a cell surface marker of said cells. Typically, the quantification of density of CD8+ T cells is performed by contacting the tumor tissue sample with a binding partner (e.g. an antibody) specific for CD8.

For example, the quantification of the density of CD8+ Gran-B+ cells is performed by contacting the tumor tissue sample with a binding partner (e.g. an antibody) specific for a cell marker of said cells. Typically, the quantification of density of CD8+ Gran-B+ T cells is performed by contacting the tumor tissue sample with both binding partners (e.g. an antibody) specific for CD8 (cell surface marker) and Granzyme-B (intracytoplasmic marker), respectively.

Typically, the density of Treg cells or TLS-mature DC or Tconv cells, CD8+ T cells, or CD8+ Gran-B+ T cells is expressed as the number of these cells that are counted per one unit of surface area of tissue sample, e.g. as the number of cells that are counted per mm$^2$ of surface area of tumor tissue sample. In some embodiments, the density of cells may also consist of the percentage of the specific cells per total cells (set at 100%). As TLS-B cells are organized into a cell aggregate in the B-cell follicle of TLS, the density of TLS-B cells can be measured as a total surface of B-cell follicles per one unit of surface area of the tumor, e.g. as the surface area of B-cell follicles in mm$^2$ per intermediate-power field (original magnification ×100) or mm$^2$ of surface area of the tumor.

Immunohistochemistry typically includes the following steps i) fixing the tumor tissue sample with formalin, ii) embedding said tumor tissue sample in paraffin, iii) cutting said tumor tissue sample into sections for staining, iv) incubating said sections with the binding partner specific for the marker, v) rinsing said sections, vi) incubating said section with a secondary antibody typically biotinylated and vii) revealing the antigen-antibody complex typically with avidin-biotin-peroxidase complex. Accordingly, the tumor tissue sample is firstly incubated the binding partners. After washing, the labeled antibodies that are bound to marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. Hematoxylin & Eosin, DAPI, Hoechst. Other staining methods may be accomplished using any suitable method or system as would be apparent to one of skill in the art, including automated, semi-automated or manual systems. For example, one or more labels can be attached to the antibody, thereby permitting detection of the target protein (i.e. the marker). Exemplary labels include radioactive isotopes, fluorophores, ligands, chemiluminescent agents, enzymes, and combinations thereof. In some embodiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e g luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. $^3$H, $^{14}$C, $^{32}$P, $^{35}$S or $^{125}$I) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In other examples, the antibody can be conjugated to peptides or proteins that can be detected via a labeled binding partner or antibody. In an indirect IHC assay, a secondary antibody or second binding partner is necessary to detect the binding of the first binding partner, as it is not labeled. The resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the marker in the sample, or the absolute number of cells positive for the maker of interest, or the surface of cells positive for the maker of interest. Various automated sample processing, scanning and analysis systems suitable for use with IHC are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549). The image can be quantitatively or semi-quantitatively analyzed and scored based on staining intensity of the sample. Quantitative or semi-quantitative histochemistry refers to method of scanning and scoring samples that have undergone histochemistry, to identify and quantitate the presence of the specified biomarker (i.e. the marker). Quantitative or semi-quantitative methods can employ imaging software to detect staining densities or amount of staining or methods of detecting staining by the human eye, where a trained operator ranks results numerically. For example, images can be quantitatively analyzed using a pixel count algorithms and tissue recognition pattern (e.g. Aperio Spectrum Software, Automated QUantitatative Analysis platform (AQUA® platform), or Tribvn with Ilastic and Calopix software), and other standard methods that measure or quantitate or semi-quantitate the degree of staining; see e.g., U.S. Pat. Nos. 8,023,714; 7,257,268; 7,219,016; 7,646,905; published U.S. Patent Publication No. US20100136549 and 20110111435; Camp et al. (2002) Nature Medicine, 8:1323-1327; Bacus et al. (1997) Analyt Quant Cytol Histol, 19:316-328). A ratio of strong positive stain (such as brown stain) to the sum of total stained area can be calculated and scored. The amount of the detected biomarker (i.e. the marker) is quantified and given as a percentage of positive pixels and/or a score. For example, the amount can be quantified as a percentage of positive pixels. In some examples, the amount is quantified as the percentage of area stained, e.g., the percentage of positive pixels. For example, a sample can have at least or about at least or about 0, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 40%, 45%, 50%, 55%, 60%, 65%, 70%, 75%, 80%, 85%, 90%, 95% or more positive pixels as compared to the total staining area. For example, the amount can be quantified as an absolute number of cells positive for the maker of interest. In some embodiments, a score is given to the sample that is a numerical representation of the intensity or amount of the histochemical staining of the sample, and represents the amount of target biomarker (e.g., the marker) present in the sample. Optical density or percentage area values can be given a scaled score, for example on an integer scale. Thus, in some embodiments, the method of the present invention comprises the steps consisting in i) providing one or more immunostained slices of tissue section obtained by an automated slide-staining system by using a binding partner capable of selectively interacting with the marker (e.g. an antibody as above described), ii) proceeding to digitalisation of the slides of step i) by high resolution scan capture, iii) detecting the slice of tissue section on the digital picture iv) providing a size reference grid with uniformly distributed units having a same surface, said grid being adapted to the size of the tissue section to be analyzed, and v) detecting, quantifying and measuring intensity or the absolute number of stained cells in each unit whereby the number or the density of cells stained of each unit is assessed.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of cell densities in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after quantifying the cell density in a group of reference, one can use algorithmic analysis for the statistic treatment of the measured densities in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGN-ROC.FOR, MULTIREADER POWER.SAS, CREATE-ROC.SAS, GB STAT V10.0 (Dynamic Microsystems, Inc. Silver Spring, Md., USA), etc.

In some embodiments, the predetermined reference value is determined by carrying out a method comprising the steps of a) providing a collection of tumor tissue samples from subject suffering from a lung cancer;

b) providing, for each tumor tissue sample provided at step a), information relating to the actual clinical outcome for the corresponding subject (i.e. the duration of the disease-free survival (DFS) and/or the overall survival (OS));

c) providing a serial of arbitrary quantification values;

d) quantifying the cell density for each tumor tissue sample contained in the collection provided at step a);

e) classifying said tumor tissue samples in two groups for one specific arbitrary quantification value provided at step c), respectively: (i) a first group comprising tumor tissue samples that exhibit a quantification value for level that is lower than the said arbitrary quantification value contained in the said serial of quantification values; (ii) a second group comprising tumor tissue samples that exhibit a quantification value for said level that is higher than the said arbitrary quantification value contained in the said serial of quantification values; whereby two groups of tumor tissue samples are obtained for the said specific quantification value, wherein the tumor tissue samples of each group are separately enumerated;

1) calculating the statistical significance between (i) the quantification value obtained at step e) and (ii) the actual clinical outcome of the subjects from which tumor tissue samples contained in the first and second groups defined at step f) derive;

g) reiterating steps f) and g) until every arbitrary quantification value provided at step d) is tested;

h) setting the said predetermined reference value as consisting of the arbitrary quantification value for which the highest statistical significance (most significant P-value obtained with a log-rank test, significance when P<0.05) has been calculated at step g).

For example the cell density has been assessed for 100 tumor tissue samples of 100 subjects. The 100 samples are ranked according to the cell density. Sample 1 has the highest density and sample 100 has the lowest density. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer subject, Kaplan-Meier curves are prepared for each of the 99 groups of two subsets. Also for each of the 99 groups, the p value between both subsets was calculated (log-rank test). The predetermined reference value is then selected such as the discrimination based on the criterion of the minimum P-value is the strongest. In other terms, the cell density corresponding to the boundary between both subsets for which the P-value is minimum is considered as the predetermined reference value. It should be noted that the predetermined reference value is not necessarily the median value of cell densities. Thus in some embodiments, the predetermined reference value thus allows discrimination between a poor and a good prognosis with respect to DFS and OS for a subject. Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P-value) are retained, so that a range of quantification values is provided. This range of quantification values includes a "cut-off" value as described above. For example, according to this specific embodiment of a "cut-off" value, the outcome can be determined by comparing the cell density with the range of values which are identified. In some embodiments, a cut-off value thus consists of a range of quantification values, e.g. centered on the quantification value for which the highest statistical significance value is found (e.g. generally the minimum P-value which is found).

In some embodiments, the method of the invention comprises comparison steps which include a classification of the quantification values measured for each cell density in two groups, as follows: (i) a first group termed "Hi" when the quantification value for cell density is higher than the predetermined corresponding reference value and (ii) a second group termed "Lo" when the quantification value for the cell density is lower than the predetermined corresponding reference value. It flows from the example that if the result of the comparison step consists of a "Hi" value for Treg cells and "Lo" value for one further population of immune cells, then a poor prognosis is provided. Conversely, if the result of the comparison step consists of a "Lo" values for Treg cells and a "Hi" value for one further population of immune cells, then a good prognosis is provided. A score which is a composite of the Treg cell densities and the further population of immune cells densities may be calculated according to the following table.

TABLE 1 scores that are composite of the Treg cell densities and the further population of immune cells densities

| Combination | Prognosis | Score |
|---|---|---|
| Hi one further population of immune cells/Lo Treg | good | 4 |
| Lo one further population of immune cells/Lo Treg | Intermediate | 3 |
| Hi one further population of immune cells/Hi Treg | Intermediate | 2 |
| Lo one further population of immune cells/Hi Treg | bad | 1 |

In some embodiments, the method of the present invention is suitable for determining whether a patient is eligible or not to a treatment, in particular an immunotherapeutic agent. For example, when it is concluded that the patient has a poor prognosis then the physician can take the choice to administer the patient with a treatment. Typically, the treatment includes chemotherapy, radiotherapy, and immunotherapy.

In some embodiments, the subject is administered with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxy uridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylamine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.]) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the subject is administered with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S. Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo [3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S. Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the subject is administered with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Amesp (erytropoietin).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen express cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

In some embodiments, the immunotherapeutic agent is an immune checkpoint inhibitor. As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2 (Pardoll, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. In some embodiments, the immune checkpoint inhibitor is an antibody selected from the group consisting of anti-CTLA4 antibodies (e.g. Ipilimumab), anti-PD1 antibodies (e.g. Nivolumab, Pembrolizumab), anti-PDL1 antibodies, anti-TIM3 antibodies, anti-LAG3 antibodies, anti-B7H3 antibodies, anti-B7H4 antibodies, anti-BTLA antibodies, and anti-B7H6 antibodies. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675,206). In some embodiments, the anti-CTLA-4 antibody is ipilimumab (also known as 10D1, MDX-D010) a fully human monoclonal IgG antibody that binds to CTLA-4. Another immune checkpoint protein is programmed cell death 1 (PD-1). Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments, the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94). In some embodiments, the immunotherapeutic treatment consists of an adoptive immunotherapy, as described by Nicholas P. Restifo, Mark E. Dudley and Steven A. Rosenberg ("Adoptive immunotherapy for cancer: harnessing the T cell response, Nature Reviews Immunology, Volume 12, April 2012). In adoptive immunotherapy, the patient's circulating lymphocytes, or tumor-infiltrated lymphocytes, are isolated in vitro, activated by lymphokines such as IL-2 and readministered (Rosenberg et al., 1988; 1989). The activated lymphocytes are most preferably be the patient's own cells that were earlier isolated from a blood sample and activated (or "expanded") in vitro.

In some embodiments, the immunotherapeutic treatment consists of allografting, in particular, allograft with hematopoietic stem cell HSC. The immunotherapeutic treatment may also consist in an adoptive immunotherapy, as described by Nicholas P. Restifo, Mark E. Dudley and Steven A. Rosenberg ("Adoptive immunotherapy for cancer: harnessing the T cell response, Nature Reviews Immunology, Volume 12, April 2012). In adoptive immunotherapy, the subject's circulating lymphocytes, NK cells, are isolated amplified ex vivo and readministered to the subject. The activated lymphocytes or NK cells are most preferably be the subject's own cells that were earlier isolated from a blood or tumor sample and activated (or "expanded") ex vivo.

In some embodiments, the subject is administered with a radiotherapeutic agent. The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

The invention will be further illustrated by the following figures and examples. However, these examples and figures should not be interpreted in any way as limiting the scope of the present invention.

FIGURES

FIG. 1: High density of tumor infiltrating Tregs is associated with poor clinical outcome of the lung cancer patients. Immunostainings were performed on the 243 paraffin-embedded NSCLC tumor sections. The automatic countings performed on the stained and scanned tissue images. The Kaplan-Meier survival graphs plotted for the determination of the percentage OS of NSCLC patients. The Log-rank test used to determine the statistical significance of the data. A: The graph shows the survival curve based on the density of the FoxP3+ Tregs. High density of the Tregs is related to the poor survival of the patients (P=0.0049). B: for n=100 patients, the FoxP3+ Tregs counted in the TLS areas of the tumors separately. The patients with Tregs in the TLS areas stratified according to the, hi and low group and survival determined. The high density of the Tregs in TLS is associated with the poor survival of the patients (P=0.0245). C,E,G; The density of the Dc-lamp+ mature DC, CD20+B cells, and CD8+ T cells determined using the serial sections of the tissues and the density was found to be associated with good clinical outcome of the patients (P=0.0002, P=0.0020, and P=0.0027, respectively). D, F,H; when the density of the DC-Lamp+ mature DC, CD20+ B cells and CD8+ T cells combined with the density of the FoxP3+ Tregs, the patients could be stratified into 4 different groups (P<0.0001, P<0.0001, and P=0.0002, respectively).

FIG. 2: Determination of optimal cutoff values for the discrimination of the high and low groups based on densities of the CD3+ T cells, FoxP3+ Tregs, ratio of CD3+ T cells or CD8+ T cells or mature DC with the Tregs, and finally the density of TLS-Tregs Optimal cut-off values are 898.793 CD3+FoxP3− Tconv (A), 21.997 CD3+FoxP3+ Tregs (B), 17.94117 CD3+ Tconv/Tregs (C), 12.41506 CD8+ T cells/Tregs (D), 0.06297162 DC-Lamp+ mature DC/Tregs (E), and 127.0348 TLS-Tregs (F).

FIG. 3: Kaplan Meier curves for the total CD3+ T cells and the ratio of the CD3+ T cells, CD8+ T cells and mature DC with Tregs, respectively. Immunostainings were performed on the 243 paraffin embedded NSCLC tumor sections. The automatic countings performed on the stained and scanned tissue images. The Kaplan-Meier survival graphs plotted for the determination of the percentage OS of the patients. The Log-rank test used to determine the statistical significance of the data. A: The graph shows the survival curve based on the density of the total CD3+ T cells. High density of the CD3+ T cells is related to the good survival of the patients (OS, CD3 Hi 92 months versus OS CD3 low 41 months P=0.0073). B: The high ratio of the CD3+ T cells/FoxP3+ Tregs is beneficial for the patients (OS=92 months) versus the low ratio (OS=40 months, P=0.0008) C; The high ratio of the mature DC cells/FoxP3+ Tregs is gives good prognosis for the patients versus the low ratio (OS=46 months, P=0.0003), D; The high ratio of the CD8+ T cells/FoxP3+ Tregs is gives good prognosis for the patients versus the low ratio (OS=41 months, P=0.0005).

FIG. 4: High density of tumor-infiltrating Tregs is associated with poor clinical outcome of the lung cancer patients and when combined with DC-Lamp+ DC and CD8+ T cells, allows identification of patients with high risk of death. Immunostainings were performed on the 338 paraffin-embedded NSCLC tumor sections. The Kaplan-Meier survival graphs were plotted for the determination of the OS of the NSCLC patients. The log-rank test was used to determine the statistical significance of the data. (A) The FoxP3+ Tregs were counted in the tumor areas (n=338 patients). (B) The FoxP3+ Tregs were also counted in the TLS areas of the tumors separately (n=100). The patients were stratified into high and low groups according to Tregs density and survival determined. (C, E, G) The densities of CD3+ T cells, CD8+ T cells and DC-Lamp+ mature DC were also determined using serial sections of tissues. (D, F, H) When the densities of CD3+ T cells, CD8+ T cells and DC-Lamp+ mature DC were combined with the density of the FoxP3+ Tregs, the patients could be stratified into 4 different groups (P<0.001 in all three cases). The table below each Kaplan Meier curve graph shows the number of patients at risk, number of events and censored according to the cell density group. Tables also show the 24, 60 and 120 months OS rates (%) according to the group of patients respectively.

FIG. 5: High density of tumor-infiltrating Tregs is associated with poor clinical outcome of the lung cancer patients and when combined with TLS-B cells or $CD8^+$ Granzyme-$B^+$ T cells, allows identification of patients with high risk of death. Immunostainings were performed on the 338 paraffin-embedded NSCLC tumor sections. The Kaplan-Meier survival graphs were plotted for the determination of the OS of the NSCLC patients. The log-rank test was used to determine the statistical significance of the data. Total $FoxP3^+$ $CD3^+$ Tregs were either counted on the whole tumor section (A,C; n=338 tumors), or selectively on TLS (called "TLS-Tregs", B,D; n=100 tumors). Tumor-infiltrating $CD20^+$ B cells (TLS-B cells) were selectively counted on TLS, and tumor-infiltrating $CD8^+$ Granzyme-$B^+$ T cells on the whole tumor section using serial sections of tissues. The patients were stratified into high (Hi) and low (Lo) groups according to the immune population density, and survival determined. The combination of TLS-B cells with total Tregs (A), TLS-B cells with TLS-Tregs (B), CD8$^+$ Granzyme-B$^+$ T cells with total Tregs (C), and CD8$^+$ Granzyme-B' T cells with TLS-Tregs (D) gives rise to 4 groups of NSCLC patients. The number of patients per group is mentioned in brackets.

EXAMPLE

Material & Methods:
Patients:

After complete surgical resection, primary lung tumor samples were obtained from the NSCLC patients at Institut Mutualiste Montsouris, Hotel Dieu and Cochin hospitals (Paris, France). A retrospective cohort of 243 NSCLC patients from Hotel Dieu Hospital (Paris) operated between year 2001 to 2005 was enrolled in this study. Patients treated with neoadjuvant chemotherapy and radiotherapy was excluded from this cohort. A time between the surgery and last follow up or death is considered as the observation time for this cohort. The data on long-term outcomes were obtained after interaction from municipality registers or the family of the patient. This protocol was approved by the local ethical committee (no 2008-133 and no 2012-0612) an application with the article L.1121-1 of French law. For prospective cohort, the fresh tumor biopsies were obtained from 55 NSCLC patients. The non-tumoral distant lung specimen (NTDL) and lymph node (LN) specimen were also obtained from the patients undergoing surgery. Samples were obtained from patients with written consent. The main clinical and pathological features of the patients for retrospective and prospective cohorts are presented in the Tables 2 and 3, respectively.

TABLE 2

Clinical and pathological characteristics of the retrospective cohort of NSCLC patients.

| Characteristics | No. | % |
|---|---|---|
| Gender | | |
| Male/female | 191/52 | 79/21 |
| Age | | |
| Mean (years) +/− SEM | 62.6 +/− 0.7 | |
| Range | 19-83 | |
| Smoking history | | |
| Current | 200 | 82 |
| Never smokers | 31 | 13 |
| ND | 12 | 5 |
| Pack-years (years) +/− SEM | 42.5 +/− 1.6 | |
| Range | 0-120 | |
| Histological type | | |
| ADC | 141 | 58 |
| SCC | 61 | 25 |
| Others | 8 | 3 |
| ND | 33 | 14 |
| Emboli | | |
| No | 77 | 32 |
| Yes | 125 | 51 |
| ND | 41 | 17 |
| pT stage | | |
| T1 | 52 | 21 |
| T2 | 118 | 49 |
| T3 | 56 | 23 |
| T4 | 17 | 7 |
| ND | 0 | 0 |
| pN stage | | |
| N0 | 156 | 64 |
| N1 | 44 | 18 |
| N2 | 43 | 18 |
| ND | 0 | 0 |
| pM stage | | |
| M0 | 242 | 100 |
| M1 | 1 | 0 |
| ND | 0 | 0 |
| pTNM stage | | |
| I | 108 | 44 |
| II | 63 | 26 |
| III | 71 | 29 |
| IV | 1 | 1 |
| ND | 0 | 0 |
| Vital status of patients | | |
| Alive | 95 | 39 |
| Dead | 148 | 61 |

All parameters were evaluated among 243 NSCLC patients. Pathologic staging of lung cancer was determined according to the new TNM staging classification46. Histological subtypes were determined according to the classification of the WHO47.
Abbreviations:
ADC, adenocarcinoma;
ND, not determined;
SCC, squamous cell carcinoma

TABLE 2

Clinical and pathological characteristics of the prospective cohort of NSCLC patients.

| Characteristics | No. | % |
|---|---|---|
| Gender | | |
| Male/female | 33/22 | 60/40 |
| Age | | |
| Mean (years) +/− SEM | 67.5 +/− 1.3 | |
| Range | 48-91 | |
| Smoking history | | |
| Current | 32 | 58 |
| Never smokers | 13 | 24 |
| ND | 10 | 18 |
| Pack-years (years) +/− SEM | 37.3 +/− 4.5 | |
| Range | 0-140 | |
| Histological type | | |
| ADC | 33 | 60 |
| SCC | 13 | 24 |
| Others | 7 | 13 |
| ND | 2 | 3 |
| pT stage | | |
| T1 | 7 | 13 |
| T2 | 36 | 65 |
| T3 | 10 | 18 |
| T4 | 1 | 2 |
| ND | 1 | 2 |
| pN stage | | |
| N0 | 33 | 60 |
| N1 | 10 | 18 |
| N2 | 9 | 16 |
| ND | 3 | 6 |

TABLE 2-continued

Clinical and pathological characteristics of
the prospective cohort of NSCLC patients.

| Characteristics | No. | % |
|---|---|---|
| pTNM stage | | |
| I | 23 | 42 |
| II | 17 | 31 |
| III | 12 | 22 |
| IV | 0 | 0 |
| ND | 3 | 5 |

All parameters were evaluated among 55 NSCLC patients. Pathologic staging of lung cancer was determined according to the new TNM staging classification46 Histological subtypes were determined according to the classification of the WHO47.
Abbreviations: ADC, adenocarcinoma; ND, not determined; SCC, squamous cell carcinoma.

Immunohistochemistry:

Formalin fixed, paraffin-embedded tissue serial sections with 5 µm thickness were used for immunohistochemistry double staining for CD3, FoxP3, DC-Lamp, CD8, CD20, CD21, and pan-cytokeratins. Briefly, tissue sections were deparaffinized, rehydrated and treated with the antigen retrieval buffer TRS (Dako). The sections were incubated in the protein bloc (Dako) for 30 min before the addition of the appropriate primary and secondary antibodies. The enzymatic activity was performed using substrate kits. Images were acquired using Nanozoomer (Hamamatsu) with NDPview software.

Cell Quantification:

Immune cells were quantified in the whole tumor section using Calopix software (Tribvn), and expressed as a number of cells/mm2 of the areas of interest. The surface area of the region of interest was also determined using the same software. The region of TLS was determined manually referring the double DC-Lamp/CD3 (T-cell zone of TLS) and CD20/CD21 (B-cell zone of TLS) staining. The density of CD3+FoxP3+ cells in TLS was determined with automatic counting. The quantification of the TLS-DC-Lamp+ DC, CD3+ T cells, CD8+ T cells, TLS-CD20+ B cells was determined, as previously described 7(22).

Flow Cytometry:

A total of 34 NSCLC fresh tumor samples were enrolled in this study. Tumoral and non-tumoral tissue specimens were mechanically dilacerated and digested in a non-enzymatic solution (cell recovery solution, BD Biosciences). The total mononuclear cells were obtained after a ficoll gradient. Mononuclear cells were stained with multiple panels of the fluorescently conjugated antibodies and their matched isotype controls. Further, cells were fixed and permeabilized using fix/perm kit (ebioscience) for intracellular stainings. Cells were washed, and data acquired on the Fortessa cytometer (BD Biosciences). Data were analyzed using flow Jo 9.7.6 (Tree Star Inc, Ashland, Oreg.) and Spice 5.3.5 (developed by Mario Roederer, Vaccine Research Center, NIAID, NIH) software programs.

Cell Sorting:

Four populations of cells, namely CD62L+ and CD62L− Tregs, CD62L+ and CD62L-CD4+ conventional T cells (Tconv) were sorted from fresh tumor and non-tumoral tissue specimens (n=20) using the in house designed protocol. Briefly, the combinations of Easysep™ untouched human CD4+ T cell kit (stem cell technologies Ref. No.) and flow cytometry cell sorting were used to achieve the high purity of the cell subsets. The cells were sorted directly into vials containing RLT+ 10% β-mercaptoethanol in order to obtain the best quality and quantity of the mRNA.

RNA Extraction and Reverse Transcription:

Total mRNA from the sorted cells was extracted with the RNeasy micro kit (Qiagen) according to manufacturer's instructions, and RNA quantity and quality were determined using the 2100 Bioanalyzer (Agilent Technologies). The mRNA was reverse transcribed to cDNA using a superscript VILO kit (Life Technologies). The samples below 1 ng of mRNA were amplified by 9 cycles, and samples with more than 1 ng of mRNA were amplified by 7 cycles of PCR using Taqman PreAmp 2× and MTE primers (NanoString technologies, Seatle, USA).

Gene Expression Analysis:

The gene expression was performed using the nCounter analysis system (Nanostring Technologies). Two specific probes (capture and reporter) for each gene of interest were applied. The customized reporter probe and capture probe code-set of selected 125 genes, including 5 housekeeping controls (β-actin, GAPDH, EEF1G, OAZ1 and RPL19) and cell lineage controls (CD3, CD4, CD8, CD19, CD138 and EpCAM) were used for the hybridization according to the manufacturer's instructions (Nanostring Technologies, Seattle, USA). Water was used as a negative control to check the background noise. The hybridized samples were recovered using the NanoString Prep-station and the mRNA molecules counted with the digital nCounter. The number of counts represented the expression of genes. The positive and negative controls, and one patients RNA sample as internal control, were used to check the technical consistency during different batch of experiments.

Statistical Analysis:

Mann-Whitney U test and Wilcoxon Rank test ($P<0.05*$, $P<0.01$, $P<0.001*$) was used to compare the density of cells in the different tumors. The overall survival (OS) curves were estimated by the Kaplan-Meier method, and differences between groups of patients were calculated using log-rank test. Patients were stratified into two groups according to the high and low densities of immune cells using "minimum P-value" approach, as previously published (7,22). Optimal cut-off values are 898.793 CD3+ FoxP3− Tconv, 21.997 CD3+FoxP3+ Tregs, 127.0348 TLS Tregs, 1.248 DC-Lamp+DC, 226.5 CD8+ T cells/mm2, and 0.3256% TLS-CD20+ B cells of tumor areas (FIG. 2). All analyses were performed with Prism 5 (GraphPad), Statview (Abacus system) and R (http://www.r-project.org/) softwares. For gene expression study and heatmap demonstrations, the softwares 'nSolver' (Nanostring Technologies) and R were used. The Raw data were normalized with an average count of the 5 housekeeping genes using "nSolver" software. The Student T test and ANOVA test were used to compare the gene expression among the groups of data, respectively. To avoid the inclusion of the false positive results, we computed the P-values with false discovery rate (FDR) method. The data were represented in the Heatmap, volcano plot, and correlation matrix format.

Results

Tregs Infiltrate Different Areas of Lung Tumors Comprising TLS, and Exhibit an Activated Memory Phenotype We evaluated the presence, localization, and frequency of tumor-infiltrating Tregs in NSCLC patients. The presence of CD3+FoxP3+ T cells was detected in different tumor areas by immunohistochemistry. Rare CD3+FoxP3+ T cells were observed in tumor beds, as for the other T cell subsets like CD8+ T cells. Indeed, the majority of T cells among with CD3+FoxP3+ and CD8+ T cells were detected in the tumor stroma. A deeper characterization of the stroma reaction allowed us to visualize Tregs in the T-cell rich areas of TLS, as demonstrated by the presence of DC-Lamp+ mature DC and CD3+ T cell clusters.

Next, we deciphered the phenotype of CD3+FoxP3+ T cells infiltrating tumors as well as non-tumoral distant sites by multicolor flow cytometry. We observed that this population exclusively expressed CD4 (not CD8), high level of CD25, and were CD127−/Lo. This observation was concordant to the phenotype of human natural CD4+ Tregs demonstrated in the literature (23,24). Even with a heterogeneity of CD3+FoxP3+ Tregs among NSCLC patients, the percentage of Tregs among total CD4+ T cells was always higher in tumor (14.49+1.34%) compared to their percentage in NTDL (4.98+0.63%), LN (8.24+0.95%), and peripheral blood (6.26+1.48%) suggesting an active recruitment of this T cell subset in tumor. Since CD62L is a specific marker of TLS-T cells (7,25), we next studied and compared the stage of differentiation of Tregs versus CD4+ Tconv in TLS (CD62L+) versus non-TLS areas (CD62L−) of the tumor. A minority of Tregs home into tumor-induced TLS (28.90+4.58% of CD3+CD4+CD25++FoxP3+CD62L+/total Tregs as observed for CD4+ Tconv (16.07+4.58% of CD3+CD4+CD62L+/total CD4+ Tconv (excluding Tregs). Based on the differential expression of CCR7, CD45ra, CD27, and CD28, TLS-Tregs were mainly of central memory (CM) and effector-memory type 1 (EM1) phenotype; and even rare, all naïve Tregs were detected in TLS, as observed for CD4+ Tconv. However, substantial differences were observed regarding the frequency of Tregs compared to CD4+ Tconv with less naïve and CM, and more EM1 Tregs than CD4+ Tconv in TLS. Same predominant stages of differentiation were detected for Tregs and CD4+ Tconv in non-TLS areas but with a different distribution. Indeed, non-TLS Tregs were mainly of EM1 phenotype, and to a lesser extent, CM and EM4 whereas these three stages were equally distributed among CD4+ T cony. Of note, no terminal EM (TEMRA) Tregs (CCR7− CD45ra+) were detected in the tumor. Interestingly, the analysis of the distribution of the four T cell stages in tumor and non-tumoral distant sites (NTDL, LN, and blood) indicated that the phenotype of Tregs is the same in tumor and NTDL which is distinct to LN and blood, the main difference was the frequency of CM and EM populations.

Altogether, Tregs infiltrate different tumor areas along with TLS, with distinct stages of differentiation suggesting that they may exhibit distinct function, accordingly.

Tregs Exhibit an Activated Phenotype and a Distinct Gene Signature Compared to the Conventional CD4+ T Cells in Tumor The presence of different stages of Treg differentiation in distinct tumor areas led us to investigate the nature of their activation, immunosuppression, and immune checkpoint (ICP) status. Thus, the expression of activation and immunoregulation markers was investigated at the molecular (n=169) and protein (n=14) level on Tregs, and compared their phenotype to the one of CD4+ Tconv in tumors. Along with the FoxP3, IL2Rα and IL2Rβ, tumor-infiltrating Tregs significantly over-expressed some transcription factors (Helios and IRF4), chemokine (CCL22) and receptors (CXCR3, CCR4, and CCR8), cytokines (IL10, IL27, and IFNα) and receptors (TNFR2, IL1R1, and IL1R2), activation receptors (GITR, 4-1BB, ICOS and OX40), and several ICP molecules (membrane and soluble CTLA-4, LAG-3, Tim-3, TIGIT, CD39, B7H3, GARP, and PDL2) compared to the CD4+ Tconv. In accordance with the gene expression level, the percentage of Tregs positive for GITR, ICOS, 4-1BB, OX40, CTLA-4, Tim-3, and TIGIT at the protein level was remarkably higher than the CD4+ Tconv whereas no statistical differences was measured for LAG-3 between the two T cell subsets.

Because, TLS is considered as the privileged sites for the activation of the T cells, we next compared the gene expression profile of Tregs versus CD4+ Tconv, according to TLS presence. Genes significantly over-expressed on Tregs were similar in TLS and non-TLS. However, few specificities can be noticed in TLS (Tim-3, IL6, CCR5, and CXCR3), and non-TLS (ICOS-L, PDL2, B7H3, GATA3, and FoxA1) suggesting that Tregs in TLS and non-TLS may share common regulatory functions.

In conclusion, Tregs exhibit a specific molecular pattern including activation and ICP molecules compared to CD4+ Tconv in tumor.

Functional Orientation of Tumor-Infiltrating Tregs is Remarkably Different than their Counterparts from Blood but not from NTDL Because most Tregs were of memory phenotype with putative effector function in the different sites but they prevalently infiltrated tumors, we determined whether they present the same molecular pattern whatever their localization. As previously performed, we compared the gene and protein expression level of activation, immunosuppressive and ICP markers on Tregs infiltrating tumors, NTDL, LN, and blood of NSCLC patients. Surprisingly, very few genes (11 out of 120 genes tested) were differentially expressed by Tregs in tumors versus NTDL indicating that they present a similar gene expression signature in tumoral and non-tumoral lung. Most of these genes are related to chemotaxis and ICP (PD-1, BTLA, B7-H3,IL-27,BCL6, STAT4, CD44). When comparing Tregs in tumors versus LN, we observed more over-expressed genes (n=21 among with 17 in tumors and 4 in LN), and most of them was already identified when comparing Tregs versus CD4+ Tconv in tumors. The most important number of genes differentially expressed on Tregs was between tumors versus blood. Except one, all of them were over-expressed in tumors, and include the previous highlighted genes (tumors versus LN). The tumor-associated genes in tumoral Tregs are related to transcription factors (FoxP3, FoxA1, STAT4), activation (ICOS, GITR, Ox-40, 4-1BB, TNFR2, CD26), ICP (mCTLA4, PD1, PDL1, B7-H3, BTLA, TIGIT, Tim3, LAG-3), chemotaxis (CCL20, CCL22, CXCL5, CX3CL1, CXCR3, CD200, CX3CR1, LTβR), immunosuppression (IL-10, CD39, GARP), and cytotoxic (granzyme B, granulysine, FasL) molecules. At the protein level, we confirmed that Tregs in the different sites did not express the same set of activation and ICP molecules, blood showing the most important difference with tumors. Flow cytometry analysis allowed us the study the potential concomitant expression of the studied markers. Thus, the multi-analysis of CD38, CD40L, CD69, and GITR expression shows that the percentage of Tregs negative for all these molecules strongly decreased from 80% in blood to 8% in the tumors. The percentage of Tregs expressing 1 or 2 markers was quite stable in all sites (around 60%), except in blood where it dropped to 20%. Thus, the frequency of Tregs positives for 3 to 4 markers dramatically increased from 0% in blood to 35% in tumors. Analysis of cells expressing at least 2 molecules indicates that, in most cases, single positive cells are mainly CD69 (except for blood with a preferential CD38 expression), double positive cells are CD69 and GITR, and triple positive cells are CD69, GITR and CD38. The same scenario occurred for the expression of 4.1BB, ICOS, and OX40. The proportion of triple negative Tregs significantly decreased from 65% in blood to 26% in tumors whereas it increased from 2% to 22% for triple positive Tregs. In most cases, ICOS was expressed first, followed by OX40 and then 4.1BB from single to triple positive cells. As for activation markers, the percentage of Tregs expressing none of the ICP dramatically dropped from 56% in blood to 10% in tumors. Same results for Tregs expressing one marker only. In contrast, the frequency of cells positive for at least 2 markers significantly increased from 8% in blood to 70% in tumors. TIGIT, then Tim-3 or CTLA-4 was sequentially expressed by Tregs.

Altogether, lung Tregs exhibit a specific gene pattern compared to distant sites i.e. LN and blood. And, lung cancer microenvironment is mainly infiltrated by Tregs expressing activation and ICP molecules whereas the blood Tregs rather shows a resting state.

Figure 1A:
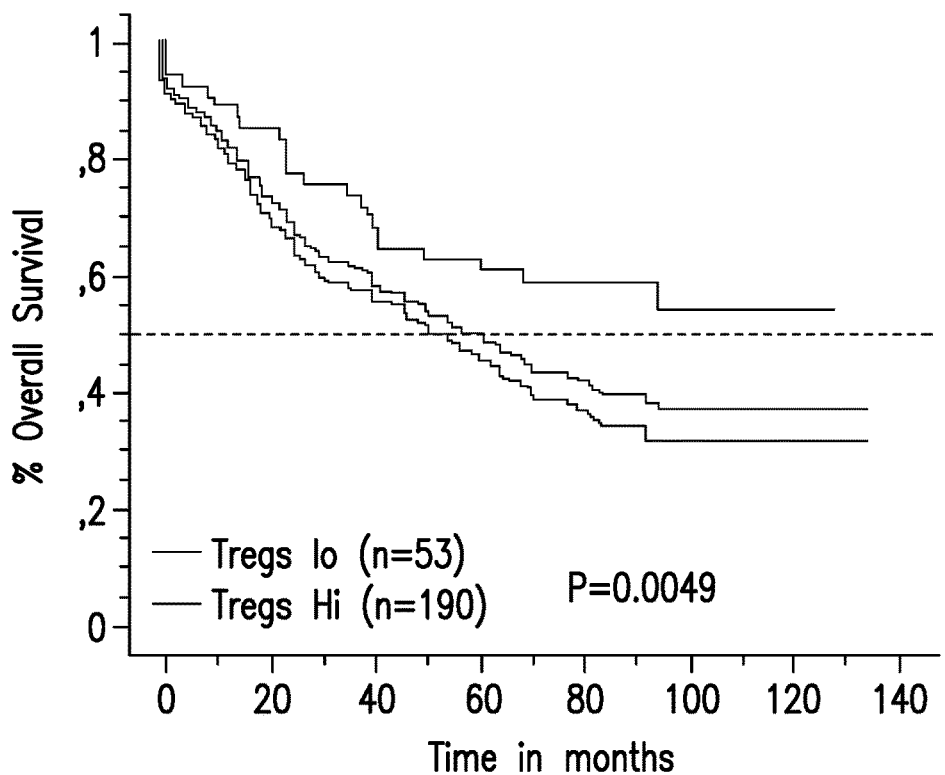
Figure 1B:
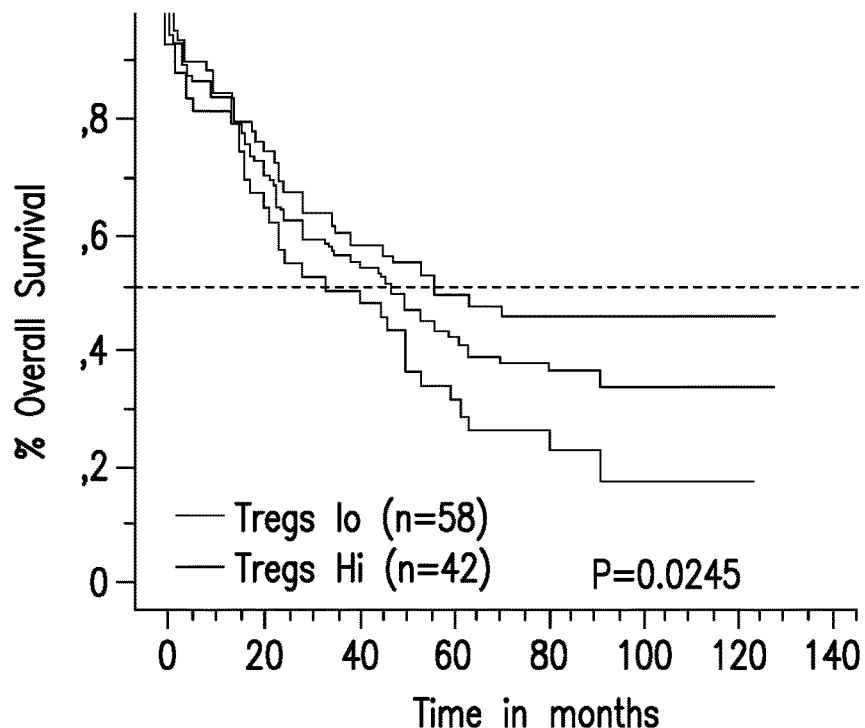
Figure 1C:
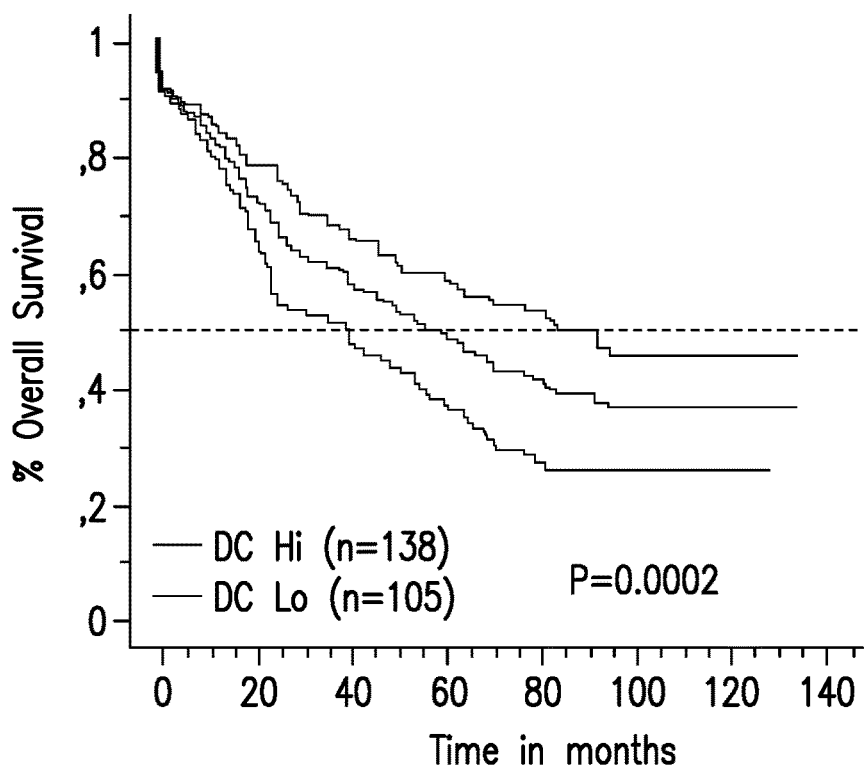
Figure 1D:
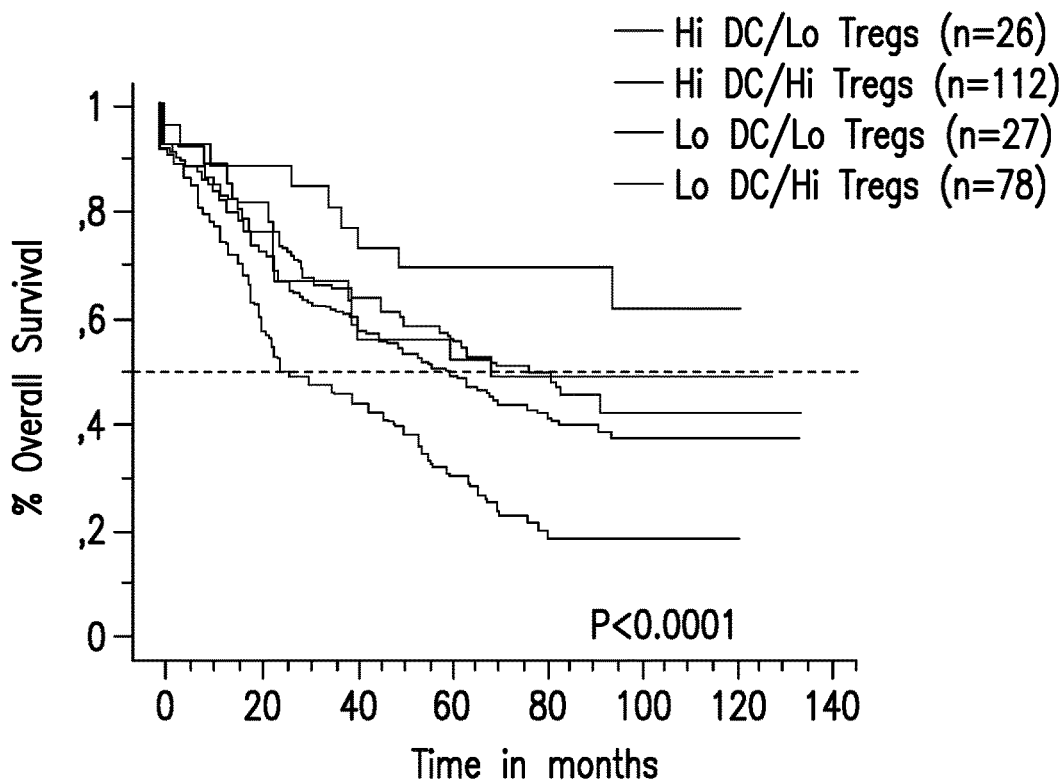
Figure 1E:
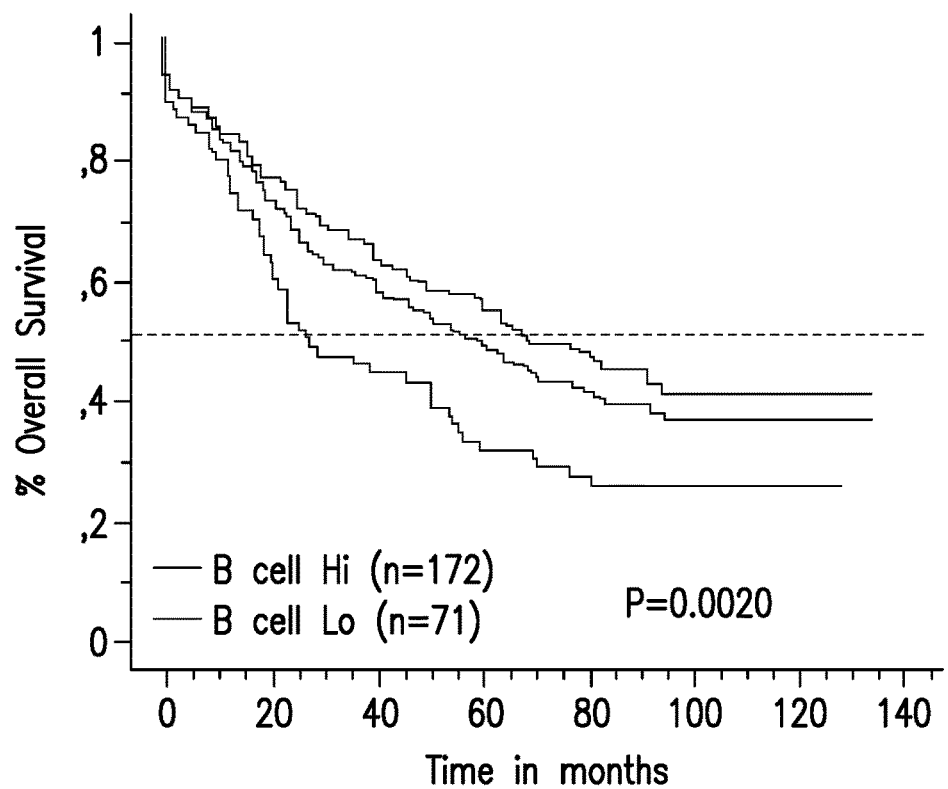
Figure 1F:
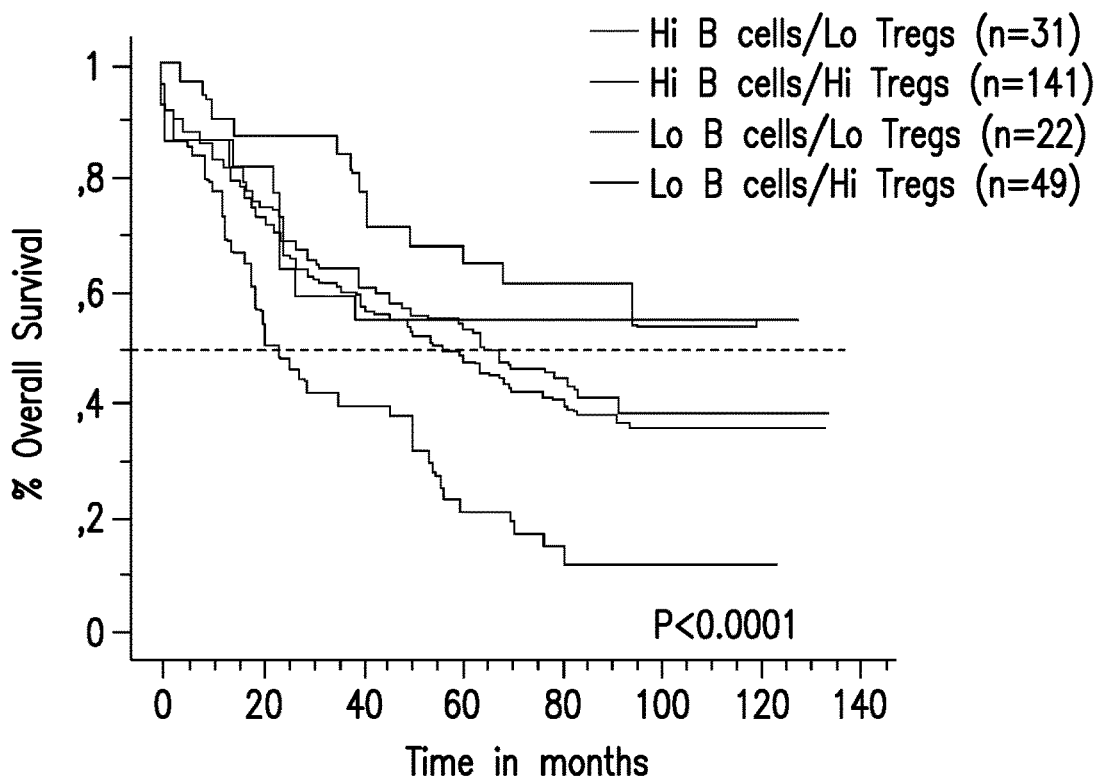
Figure 1G:
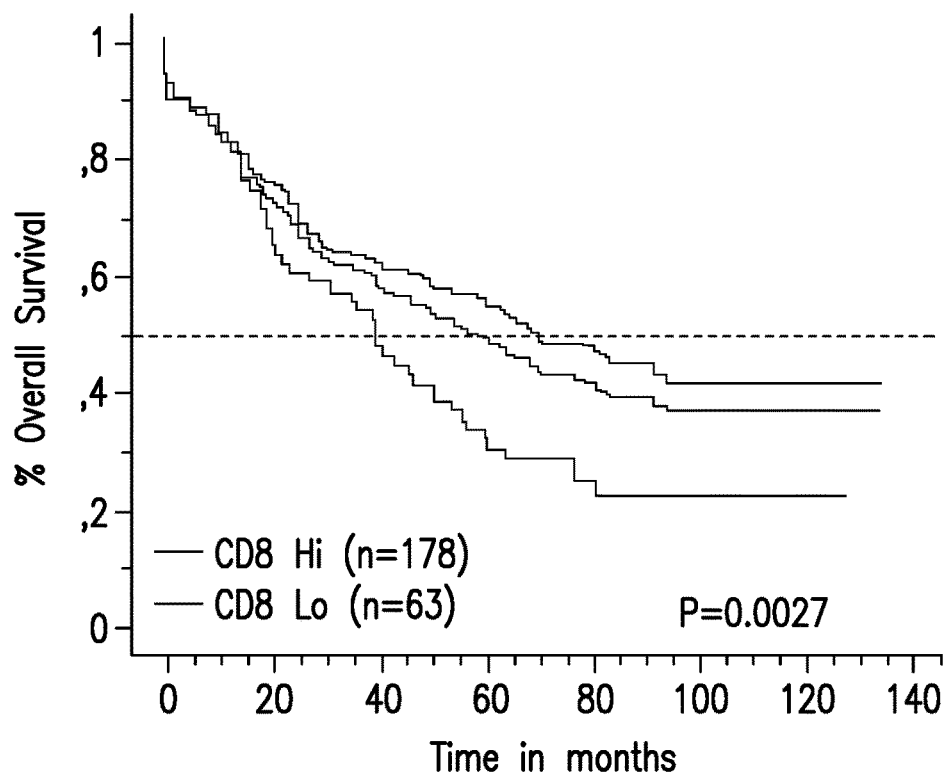
Figure 1H:
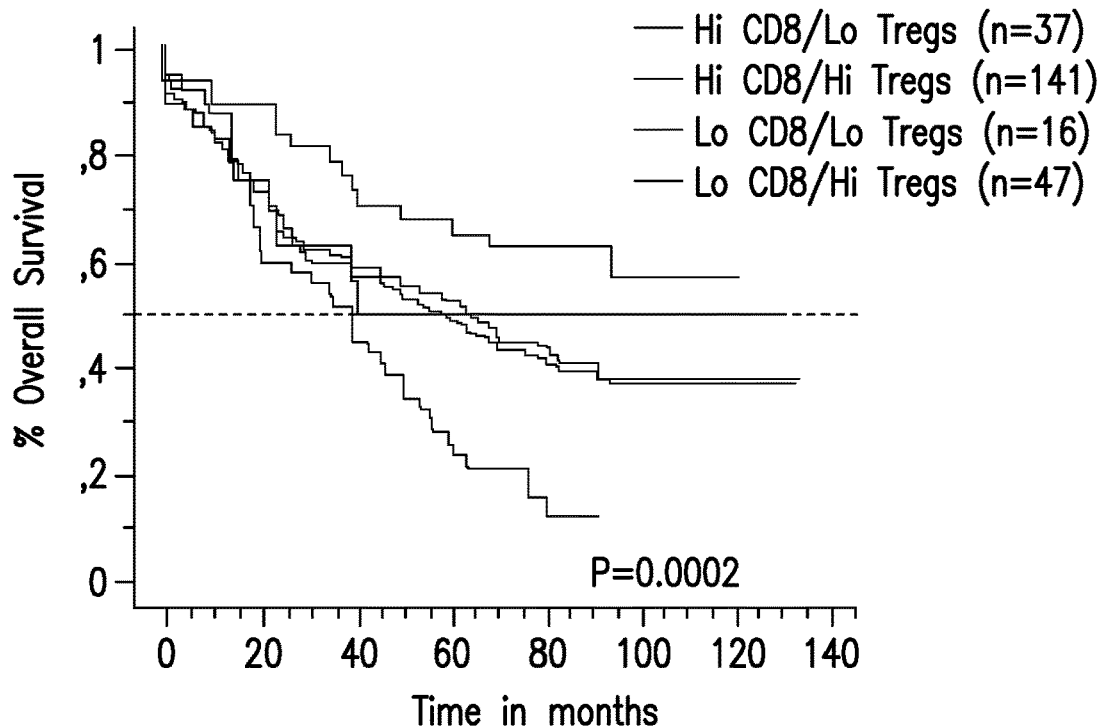

High Density of Tumor-Infiltrating Tregs is Associated with Short-Term Survival, and Combination with CD8+ T Cells, TLS-Mature DC or TLS-B Cells Allowed the Identification of Patients with the Worst Clinical Outcome The Kaplan Meier curves depict that the high density of the intra-tumoral Tregs correlated with the poor clinical outcome of NSCLC patients (median OS was not reached for "Tregs Low" whereas it was 51 months for "Tregs High" patients, P=0.0049, FIG. 1A). Since the high densities of TLS-mature DC, TLS-B cells, and effector CD8+ T cells were associated with long-term survival of patients with NSCLC 4,7,22, FIG. 1C,E,G), we further tested the combined impact of these immune cells with Tregs on patient's survival. We observed that low density of the Tregs was associated with the favorable clinical outcome whatever the density of the mature DC, TLS-B cells or CD8+ T cells. In contrast, patients having high Treg density and low mature DC (median OS=25 months; P<0.0001, FIG. 1D), TLS-B cells (median OS=24 months; P<0.0001, FIG. 1F), or CD8+ T cells (median OS=40 months; P=0.0002, FIG. 1H) density had the worst outcome with the shortest median survival compared to each variable alone. "Tregs High/mature DC, TLS-B or CD8+ T high" patients were at intermediate risk of death suggesting that, on one hand mature DC, TLS-B and CD8+ T cells, and on the other hand Tregs have a dual impact on the outcome of NSCLC patients. Since, Tregs in the different areas of the tumor have been shown to have different impact on the survival of breast cancer patients 16, we counted the Tregs in TLS and non-TLS areas separately in 100 NSCLC patients. It was observed that high densities of TLS-Tregs and non-TLS-Tregs correlated with poor clinical outcome, similar to the total Tregs (median OS=57 versus 34 months for "TLS-Tregs Low" and "TLS-Tregs High" patients, respectively; P=0.0245, FIG. 1B). We also determined the ratio of total CD3+ T cells or CD8+ T cells or mature DC/Treg densities, and it was found that "ratio High" of all these markers was beneficial for NSCLC patients compared to "ratio Low" (FIG. 3).

In conclusion, the balance between Tregs and other immune cells like mature DC, TLS-B cells, CD8+ T cells is critical for the behavior of NSCLC patients. Combination of Tregs with one of the other immune subsets allows a better stratification of patients for survival than each subset alone, with the identification of a group of NSCLC patients with a high risk of death.

Inventors have continued to work with more patients, particularly with a cohort of 338 NSCLC patients operated between years 2001 to 2005. As shown in FIGS. 4 and 5, inventors have confirmed that the presence of Tregs and other immune cells like CD3+ T cells along with CD8+ T cells, CD8+ Granzyme-B+ T cells, TLS-B cells as well as TLS-mature DC is critical for the survival of NSCLC patients. The combination of Tregs with other immune subsets allowed a better stratification of NSCLC patients for survival than each subset alone, and permitted the identification of a subgroup of patients with a high risk of death.

DISCUSSION

There are many studies in the literature which discuss the prognostic relevance of the Tregs in different solid cancers, but it has been always debatable due to various factors responsible for the discrepancy. Depending on the tumor type, stage and histological type, the prognostic importance of Tregs was found to be different (15). Based on their localization, Tregs either may suppress or help the anti-tumor responses. In germinal centers, it has been recently observed that Tregs may help the Tfh differentiation (26). Thus, it was interesting to speculate the different roles and phenotypes of the Tregs in different areas of the tumors. With the advanced techniques available, we re-addressed the prognostic value of Tregs as a total population, and also depending on their localization in the different subareas of lung tumors.

We first time demonstrated the presence of CD3+FoxP3+ T cells in the different areas of NSCLC tumors. We observed that CD3+FoxP3+ T cells are mainly found in the stroma of the tumor, and particularly TLS in the stroma; there are few CD3+FoxP3+ T cells in the tumor nests. We confirmed the CD3+FoxP3+ T cells as Tregs according to their CD4+ CD25hiCD127−/loFoxP3+ phenotype by flow cytometry, as mentioned in the literature (27,28).

Since, we observed that Tregs abundantly infiltrate the lung tumors (both TLS and non-TLS areas) compared to non-tumoral tissues, we first time studied their phenotype in detail. We observed that in general, Tregs bear the same differentiation status when compared to CD4+ Tconv7. Tumor-infiltrating Tregs predominantly show the CM and EM phenotypes. Very few naïve Tregs infiltrate tumors but interestingly, all of them home in TLS. TLS Tregs are importantly CM and EM1; whereas non-TLS Tregs showed the further differentiation phases like EM1 and EM4. Differentiation status of Tregs was not the same in tumor compared to blood or lymph node. Although Tregs exhibited similar phenotype in distant lung and tumor, there were less effector memory cells in blood and lymph node. These results initiated us to further study the activation status of the Tregs.

High infiltration of the Tregs in lung tumors (compared to the NTDL, LN and blood) is reflected by the high expression of the chemokine CCL22 and receptors like CCR8, CCR4, and CX3CL1 by intra-tumoral Tregs. We also observed the higher expression of the CXCR3 in TLS Tregs which could be possible way of their recruitment to the inflammatory site (29). Mature DC can produce CCL2230 which can recruit CCR4+ Tregs. The role of CCR4, CCL17, and CCL22 in chemoattraction of Tregs to the inflamed sites is enough discussed in mouse and human studies (16,31).

Since, the around 25% of the total intratumoral Tregs infiltrate TLS, it can be speculated that TLS-Tregs can suppress the TAA-specific T cells in the TLS as well as non-TLS areas of the tumors. When gene expression of Tregs in TLS and non-TLS areas of tumors was compared, we found a similar profile, as for total Tregs. TLS Tregs selectively expressed the molecules like Tim3, IL6, CCR5, and CXCR3 in comparison to the non-TLS Tregs which overexpressed more transcription factors GATA3, PDL2, B7H3, and ICOSL. Surprisingly, we observed an overexpression of IL-2 Rα and IL-2Rβ, co-stimulatory (ICOS, OX40, 4-1BB and GITR) and ICP (CTLA4, TIGIT, PD1 and PDL2) molecules in Tregs compared to CD4+ Tconv. This was confirmed at protein level. In last few years, it has been demonstrated the role of ICOS in the IL-10 production by Tregs (32). Expression of ICOSL and OX-40 by plasmacytoid DC is responsible for recruitment of Tregs in melanoma and breast cancer (33,34). Treatment with IL-2 in melanoma was found to be expanding the ICOS+ Treg population (35). Although the role of GITR in Tregs has been controversial, it has been found that Tregs constitutively express GITR. All Ti-Tregs expressed HLA-DR (data not shown) which suggests the contact dependent suppression mechanism used by Tregs. The TNF superfamily receptors like TNFR2, 4-1BB, and Ox-40 may help in their suppressive ability. Co-expression of GITR, OX-40, and TNFR2 along with TCR signaling has been found to favor the thymic differentiation of Tregs (36).

Most importantly, a proportion of Tregs express ICP. We found that Tregs in tumors express high levels of the CTLA4, TIGIT, Tim-3, B7-H3, PD1, and its ligands PDL1 and PDL2. Expression of the CTLA4 on Tregs, and its interaction with CD80 and CD86 molecules on APC (37), is greatly discussed. CTLA4 might trigger induction of enzyme IDO in DC's by interacting with their CD80 and CD86 38. CTLA4 and PD1 blockades has found to be effective in the melanoma (39), and is also showing the promising results in NSCLC probably due to its action on the Tregs expressing a higher level in comparison to the CD4+ Tconv. In our study, expression of the CTLA4 and TIGIT is found to be always correlated in the Ti-Tregs. Ligation of TIGIT on Tregs may inhibit pro-inflammatory responses by Th1 and Th17 (40). It is also observed now that Helios+ memory Tregs expressing TIGIT and FCRL3 are highly suppressive Tregs (41,42). We observed that Tregs in lung tumors are Helios positive and they also express other transcription factors like FoxA1 and GATA3. IRF4 expression of Tregs may suggest its role in the maintenance of the proliferation and activation of Tregs, as observed in CD8+ T cells (43).

We observed an overexpression of CD40L by CD4+ Tconv versus Tregs, especially by TLS CD4+ Tconv which can be possible consequences of T cell activation after interaction with mature DC in TLS, counteracting immunosuppression by Tregs. Surprisingly, we found an PDL2 overexpression by Ti-Tregs, especially TLS Tregs, compared to the lymph node Tregs but not differently from the NTDL and blood. It has been found that in germinal center, PD1-PDL1 ligation inhibits the CXCR5+ follicular Tregs and antibody production in vivo44 but the regulation via PDL2 is poorly studied.

Intratumoral Tregs express the IL-6, IL-10, and TGF-β which may lead to the suppression of T cell function and DC differentiation and activation. We observed that Tregs highly express the IL-27 which was speculated to be a negative regulator of Th17 differentiation in the tumor microenvironment. In another study in NSCLC patients, it is observed that IL-27 was negatively correlated with the Th17 cells and RORγt expression (45).

We observed that high Treg density correlated with shorter overall survival in NSCLC patients. Literature shows that in few cases, Tregs are associated with good, bad or no clinical outcome. In breast cancer patients, the presence of Tregs in the lymphoid aggregates is associated with the poor survival, whereas their presence in the tumors is not associated with the survival of the patients (16), but the evidences lack to show that these lymphoid aggregates are the functional TLS. We show that the presence of a high number of Tregs in TLS and whole tumor negatively impacts the survival of patients, which could be due to exclusive infiltration of Tregs in different areas of tumors mainly TLS and stroma region, the differentiation and activation of Tregs in the TLS and their immunosuppressive function against Tconv and APC. We provide the evidence of Tregs being activated in the tumors compared to the NTDL, LN and blood.

We have already demonstrated the presence and favorable role of TLS in the anti-immune response generation in lung cancer patients (4,7,22). The HEV have found to be involved in the recruitment of T cells, and mature DC have been found to be involved with activation of T cells in TLS. TLS are found to be participating in orchestrating the Th1 and cytotoxic oriented gene signature. We observed that, Tregs express T-bet probably to co-opt the transcription factor expression of the Th1 cells and may suppress the Th1 responses.

When the density of Tregs was combined with DC-Lamp+ mature DC, CD20+ TLS-B cells and CD8+ T cells, the stratification of the group with the highest survival could be determined. The ratio of the CD3+ T cells or mature DC or CD8+ T cells with Tregs found to be stronger prognosticator than each variable alone, it showed that a high proportion of T cells or mature DC compared to Tregs imprints the better survival for lung cancer patients.

REFERENCES

Throughout this application, various references describe the state of the art to which this invention pertains. The disclosures of these references are hereby incorporated by reference into the present disclosure.

1. Schreiber, R. D., Old, L. J. & Smyth, M. J. Cancer immunoediting: integrating immunity's roles in cancer suppression and promotion. Science 331, 1565-1570 (2011).
2. Pagés, F. et al. Immune infiltration in human tumors: a prognostic factor that should not be ignored. Oncogene 29, 1093-1102 (2010).
3. Fridman, W. H., Pagés, F., Sautés-Fridman, C. & Galon, J. The immune contexture in human tumours: impact on clinical outcome. Nat. Rev. Cancer 12, 298-306 (2012).
4. Dieu-Nosjean, M.-C. et al. Long-term survival for patients with non-small-cell lung cancer with intratumoral lymphoid structures. J. Clin. Oncol. 26, 4410-4417 (2008).
5. Dieu-Nosjean, M.-C., Goc, J., Giraldo, N. A., Sautés-Fridman, C. & Fridman, W. H. Tertiary lymphoid structures in cancer and beyond. Trends in Immunology 35, 571-580 (2014).
6. Germain, C., Gnjatic, S. & Dieu-Nosjean, M.-C. Tertiary Lymphoid Structure-Associated B Cells are Key Players in Anti-Tumor Immunity. Frontiers in immunology 6, 67 (2015).
7. Goc, J. et al. Dendritic cells in tumor-associated tertiary lymphoid structures signal a Th1 cytotoxic immune contexture and license the positive prognostic value of infiltrating CD8+ T cells. Cancer Res. 74, 705-715 (2014).
8. Gu-Trantien, C. et al. CD4[+] follicular helper T cell infiltration predicts breast cancer survival. J. Clin. Invest. 123, 2873-2892 (2013).
9. Hennequin, A. et al. Tumor infiltration by Tbet+ effector T cells and CD20+B cells is associated with survival in gastric cancer patients. Oncoimmunology, 0 (2015).
10. Ghiringhelli, F. Tumor cells convert immature myeloid dendritic cells into TGF—secreting cells inducing CD4+ CD25+ regulatory T cell proliferation. Journal of Experimental Medicine 202, 919-929 (2005).
11. Mizukami, Y. et al. CCL17 and CCL22 chemokines within tumor microenvironment are related to accumulation of Foxp3+ regulatory T cells in gastric cancer. Int. J. Cancer 122, 2286-2293 (2008).
12. Qin, X.-J. et al. CCL22 recruits CD4-positive CD25-positive regulatory T cells into malignant pleural effusion. Clin. Cancer Res. 15, 2231-2237 (2009).
13. Toulza, F. et al. Human T-Lymphotropic Virus Type 1-Induced CC Chemokine Ligand 22 Maintains a High Frequency of Functional FoxP3+ Regulatory T Cells. The Journal of Immunology 185, 183-189 (2010).
14. Vignali, Dario A A, Collison, L. W. & Workman, C. J. How regulatory T cells work. Nat. Rev. Immunol. 8, 523-532 (2008).
15. Badoual, C. et al. Prognostic value of tumor-infiltrating CD4+ T-cell subpopulations in head and neck cancers. Clin. Cancer Res. 12, 465-472 (2006).
16. Gobert, M. et al. Regulatory T cells recruited through CCL22/CCR4 are selectively activated in lymphoid infiltrates surrounding primary breast tumors and lead to an adverse clinical outcome. Cancer research 69, 2000-2009 (2009).
17. Eiichi Sato et al. Intraepithelial CD8+ tumor-infiltrating lymphocytes and a high CD8+/regulatory T cell ratio are associated with favorable prognosis in ovarian cancer. PNAS 102, 18538-18543 (2005).
18. Preston, C. C. et al. The ratios of CD8+ T cells to CD4+CD25+ FOXP3+ and FOXP3− T cells correlate with poor clinical outcome in human serous ovarian cancer. PLoS ONE 8, e80063 (2013).
19. Duhen, T., Duhen, R., Lanzavecchia, A., Sallusto, F. & Campbell, D. J. Functionally distinct subsets of human FOXP3+ Treg cells that phenotypically mirror effector Th cells. Blood 119, 4430-4440 (2012).
20. Hindley, J. P. et al. T-cell trafficking facilitated by high endothelial venules is required for tumor control after regulatory T-cell depletion. Cancer Res. 72, 5473-5482 (2012).
21. Martinet, L. et al. High Endothelial Venule Blood Vessels for Tumor-Infiltrating Lymphocytes Are Associated with Lymphotoxin-Producing Dendritic Cells in Human Breast Cancer. The Journal of Immunology 191, 2001-2008 (2013).
22. Germain, C. et al. Presence of B Cells in Tertiary Lymphoid Structures Is Associated with a Protective Immunity in Patients with Lung Cancer. Am J Respir Crit Care Med 189, 832-844 (2014).
23. Fontenot, J. D., Rasmussen, J. P., Gavin, M. A. & Rudensky, A. Y. A function for interleukin 2 in Foxp3-expressing regulatory T cells. Nat. Immunol. 6, 1142-1151 (2005).
24. Fehérvari, Z. & Sakaguchi, S. CD4+ Tregs and immune control. J. Clin. Invest. 114, 1209-1217 (2004).
25. Girard, J.-P. & Springer, T. A. High endothelial venules (HEVs). Specialized endothelium for lymphocyte migration. Immunology Today 16, 449-457 (1995).
26. Leon, B., Bradley, J. E., Lund, F. E., Randall, T. D. & Ballesteros-Tato, A. FoxP3+ regulatory T cells promote influenza-specific Tfh responses by controlling IL-2 availability. Nat Commun 5, 3495 (2014).
27. Roncador, G. et al. Analysis of FOXP3 protein expression in human CD4+CD25+ regulatory T cells at the single-cell level. Eur. J. Immunol. 35, 1681-1691 (2005).
28. Liu, W. et al. CD127 expression inversely correlates with FoxP3 and suppressive function of human CD4+ T reg cells. J. Exp. Med. 203, 1701-1711 (2006).
29. Redjimi, N. et al. CXCR3+ T regulatory cells selectively accumulate in human ovarian carcinomas to limit type I immunity. Cancer research 72, 4351-4360 (2012).
30. Vulcano, M. et al. Dendritic cells as a major source of macrophage—derived chemokine/CCL22 in vitro and in vivo. European Journal of Immunology 31 (2001).
31. Chaisemartin, L. de et al. Characterization of chemokines and adhesion molecules associated with T cell presence in tertiary lymphoid structures in human lung cancer. Cancer Res. 71, 6391-6399 (2011).
32. Lohning, M. et al. Expression of ICOS In Vivo Defines CD4+ Effector T Cells with High Inflammatory Potential and a Strong Bias for Secretion of Interleukin 10. Journal of Experimental Medicine 197, 181-193 (2003).
33. Faget, J. et al. ICOS-ligand expression on plasmacytoid dendritic cells supports breast cancer progression by promoting the accumulation of immunosuppressive CD4+ T cells. Cancer Res. 72, 6130-6141 (2012).
34. Aspord, C., Leccia, M.-T., Charles, J. & Plumas, J. Plasmacytoid dendritic cells support melanoma progression by promoting Th2 and regulatory immunity through OX40L and ICOSL. Cancer Immunol Res 1, 402-415 (2013).
35. Sim, G. C. et al. IL-2 therapy promotes suppressive ICOS+ Treg expansion in melanoma patients. J. Clin. Invest. 124, 99-110 (2014).
36. Mahmud, S. A. et al. Costimulation via the tumor-necrosis factor receptor superfamily couples TCR signal strength to the thymic differentiation of regulatory T cells. Nat. Immunol. 15, 473-481 (2014).
37. Wing, K. et al. CTLA-4 control over Foxp3+ regulatory T cell function. Science 322, 271-275 (2008).
38. Onodera, T. et al. Constitutive Expression of IDO by Dendritic Cells of Mesenteric Lymph Nodes: Functional Involvement of the CTLA-4/B7 and CCL22/CCR4 Interactions. The Journal of Immunology 183, 5608-5614 (2009).
39. Peggs, K. S., Quezada, S. A., Chambers, C. A., Korman, A. J. & Allison, J. P. Blockade of CTLA-4 on both effector and regulatory T cell compartments contributes to the antitumor activity of anti-CTLA-4 antibodies. J. Exp. Med. 206, 1717-1725 (2009).
40. Joller, N. et al. Treg cells expressing the coinhibitory molecule TIGIT selectively inhibit proinflammatory Th1 and Th17 cell responses. Immunity 40, 569-581 (2014).
41. Bin Dhuban, K. et al. Coexpression of TIGIT and FCRL3 Identifies Helios+ Human Memory Regulatory T Cells. J. Immunol. 194, 3687-3696 (2015).
42. Fuhrman, C. A. et al. Divergent Phenotypes of Human Regulatory T Cells Expressing the Receptors TIGIT and CD226. The Journal of Immunology (2015).
43. Man, K. et al. The transcription factor IRF4 is essential for TCR affinity-mediated metabolic programming and clonal expansion of T cells. Nature immunology 14, 1155-1165 (2013).
44. Sage, P. T., Francisco, L. M., Carman, C. V. & Sharpe, A. H. The receptor PD-1 controls follicular regulatory T cells in the lymph nodes and blood. Nature immunology 14, 152-161 (2013).
45. Duan, M. et al. Decreased IL-27 Negatively Correlated with Th17 Cells in Non-Small-Cell Lung Cancer Patients. Mediators of inflammation 2015, 802939 (2015).
46. Detterbeck, F. C., Boffa, D. J. & Tanoue, L. T. The new lung cancer staging system. Chest 136, 260-271 (2009).
47. Brambilla, E., Travis, W. D., Colby, T. V., Corrin, B. & Shimosato, Y. The new World Health Organization classification of lung tumours. European Respiratory Journal 18, 1059-1068 (2001).

The invention claimed is:

1. A method for predicting the survival time of a subject suffering from a lung cancer and treating patients with a low overall survival time, comprising the steps of:
   i) quantifying the density of CD3±FoxP3+ regulatory T (Treg) cells in a tumor-induced lymphoid structure (TLS) of a tumor tissue sample obtained from the subject, wherein identification of the CD3+FoxP3+ Treg cells is determined by immunostaining with an antibody directed against FoxP3,
   ii) quantifying the density of one further population of immune cells selected from the group consisting of TLS-mature DC, TLS-B cells, Tconv cells, CD8+ T cells and CD8+ Gran-B+ T cells in the TLS in the tumor tissue sample, wherein identification of the further population of immune cells is determined by immunostaining with an antibody directed against the selected type of immune cells,
   iii) comparing the densities quantified at steps i) and ii) with their corresponding predetermined reference values,
   iv) identifying that the subject has a low survival time and is thus a candidate for a cancer treatment when the density of Treg cells is higher than its corresponding predetermined reference value and the density of the further population of immune cells is lower than its corresponding predetermined reference value, and
   v) administering a cancer treatment to the subject identified as having a low survival time, wherein the cancer treatment is one or more of a chemotherapeutic agent, radiotherapy, a targeted cancer therapeutic and an immunotherapeutic agent.

2. The method of claim 1 wherein the density of regulatory T (Treg) cells and the density of TLS-mature DC are quantified at steps i) and ii) respectively.

3. The method of claim 1 wherein the density of regulatory T (Treg) cells and the density of TLS-B cells are quantified at steps i) and ii) respectively.

4. The method of claim 1 wherein the density of regulatory T (Treg) cells and the density of Tconv cells are quantified at steps i) and ii) respectively.

5. The method of claim 1 wherein the density of regulatory T (Treg) cells and the density of CD8+ T cells are quantified at steps i) and ii) respectively.

6. The method of claim 1 wherein the density of regulatory T (Treg) cells and the density of CD8+ Granzyme-B+ T cells are quantified at steps i) and ii) respectively.

7. The method of claim 1 wherein the subject suffers from a non-small cell lung carcinoma (NSCLC).

8. A method for predicting the survival time of a subject suffering from a lung cancer and treating the subject when identified as having a low overall survival time, comprising the steps of:
   i) quantifying the density of CD3±FoxP3+ regulatory T (Treg) cells in a tumor-induced lymphoid structure (TLS) in a tumor tissue sample obtained from the subject, wherein identification of the CD3+FoxP3+ Treg cells is determined by immunostaining with an antibody directed against FoxP3;
   ii) quantifying the density of TLS-mature DC in the TLS, wherein identification of the TLS-mature DC is determined by immunostaining with an antibody directed against TLS-mature DC;
   iii) comparing the densities quantified at steps i) and ii) with their corresponding predetermined reference values; and
   iv) identifying the subject as having a prediction of a low survival time when the density of Treg cells in i) is higher than its corresponding predetermined reference value, and the density of the TLS-mature DC in ii) is lower than its corresponding predetermined reference value, and
   v) administering a cancer treatment to the subject having the prediction of the low survival time, wherein the cancer treatment is one or more of a chemotherapeutic agent, radiotherapy, a targeted cancer therapeutic and an immunotherapeutic agent.

9. The method of claim 8, wherein the lung cancer is a non-small cell lung carcinoma.

* * * * *